United States Patent
Yoshizaki

(10) Patent No.: US 10,299,658 B2
(45) Date of Patent: May 28, 2019

(54) ENDOSCOPE SYSTEM, IMAGE PROCESSING DEVICE, IMAGE PROCESSING METHOD, AND COMPUTER-READABLE RECORDING MEDIUM

(71) Applicant: OLYMPUS CORPORATION, Hachioji-shi, Tokyo (JP)

(72) Inventor: Kazunori Yoshizaki, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 211 days.

(21) Appl. No.: 15/408,590

(22) Filed: Jan. 18, 2017

(65) Prior Publication Data

US 2017/0360275 A1  Dec. 21, 2017

Related U.S. Application Data

(63) Continuation of application No. PCT/JP2016/068443, filed on Jun. 21, 2016.

(51) Int. Cl.
*A61B 1/04* (2006.01)
*A61B 1/06* (2006.01)
(Continued)

(52) U.S. Cl.
CPC ...... *A61B 1/00009* (2013.01); *A61B 1/00045* (2013.01); *A61B 1/00055* (2013.01);
(Continued)

(58) Field of Classification Search
CPC combination set(s) only.
See application file for complete search history.

(56) References Cited

U.S. PATENT DOCUMENTS

2009/0322907 A1  12/2009  Takahashi
2010/0194871 A1*  8/2010  Komukai ............ A61B 1/00096
                                              348/68
(Continued)

FOREIGN PATENT DOCUMENTS

JP   2002034923 A   2/2002
JP   2008284305 A   11/2008
(Continued)

OTHER PUBLICATIONS

International Search Report (ISR) and Written Opinion dated Sep. 20, 2016 issued in International Application No. PCT/JP2016/068443.

*Primary Examiner* — Mohammed S Rahaman
*Assistant Examiner* — Samuel D Fereja
(74) *Attorney, Agent, or Firm* — Holtz, Holtz & Volek PC

(57) ABSTRACT

An image processing method includes: sequentially generating fluorescent image data in accordance with light intensity of a wavelength component emitted from a fluorescent agent having been administered to a subject irradiated with excitation light, based on image data of the subject each time the image data is generated; sequentially calculating a change amount of the light intensity based on two sets of temporally successive fluorescent image data each time the fluorescent image data is generated; determining whether the change amount is not less than a first threshold indicating fluorescence expression; determining whether the change amount is less than a second threshold indicating a steady state of fluorescence after the change amount is determined to be not less than the first threshold; and outputting a message that fluorescence of the fluorescent agent is in the steady state if the change amount is determined to be less than the second threshold.

12 Claims, 21 Drawing Sheets

(51) Int. Cl.
  *A61B 1/00* (2006.01)
  *G02B 23/24* (2006.01)
  *A61B 1/045* (2006.01)
  *A61B 1/07* (2006.01)
  *H04N 5/262* (2006.01)
  *H04N 5/225* (2006.01)

(52) U.S. Cl.
  CPC .............. *A61B 1/042* (2013.01); *A61B 1/043* (2013.01); *A61B 1/045* (2013.01); *A61B 1/0653* (2013.01); *A61B 1/0669* (2013.01); *A61B 1/07* (2013.01); *G02B 23/2461* (2013.01); *G02B 23/2484* (2013.01); *H04N 5/262* (2013.01); *H04N 5/2256* (2013.01); *H04N 2005/2255* (2013.01)

(56) References Cited

U.S. PATENT DOCUMENTS

| | | |
|---|---|---|
| 2011/0158914 A1 | 6/2011 | Yamada |
| 2012/0271128 A1 | 10/2012 | Kubo et al. |
| 2013/0012864 A1 | 1/2013 | Kubo et al. |
| 2017/0035280 A1* | 2/2017 | Yang ................... A61B 1/0638 |

FOREIGN PATENT DOCUMENTS

| | | |
|---|---|---|
| JP | 2010005056 A | 1/2010 |
| JP | 2011131002 A | 7/2011 |
| JP | 5294723 B2 | 9/2013 |
| JP | 5637783 B2 | 12/2014 |
| WO | 2012081336 A1 | 6/2012 |
| WO | 2012124227 A1 | 9/2012 |

* cited by examiner

FIG.3

| | | | 222a |
|---|---|---|---|
| R | G | R | G |
| G | B | G | B |
| R | G | R | G |
| G | B | G | B |

# ENDOSCOPE SYSTEM, IMAGE PROCESSING DEVICE, IMAGE PROCESSING METHOD, AND COMPUTER-READABLE RECORDING MEDIUM

CROSS-REFERENCE TO RELATED APPLICATION

This application is a continuation of International Application No. PCT/JP2016/068443 filed on Jun. 21, 2016, the entire contents of which are incorporated herein by reference.

BACKGROUND

1. Technical Field

The disclosure relates to an endoscope system, an image processing device, an image processing method, and a computer-readable recording medium for generating fluorescent image data by emitting excitation light to a subject to which a fluorescent agent has been administered.

2. Related Art

In the related art, there is a known technique in which excitation light is emitted after administering indocyanine green (ICG) to a subject by spraying or injecting, into body tissue, the ICG as a fluorescent agent that causes excitation at a specific wavelength in an endoscope, and a site and a position of a blood vessel and flow of lymph at a sentinel lymph node are observed by observing temporal change of a light emission property of the ICG (refer to JP 5294723 B).

SUMMARY

In some embodiments, an endoscope system includes: a light source unit configured to emit excitation light to a subject to which a fluorescent agent has been administered; an imaging unit configured to continuously image the subject and sequentially generate image data of the subject; a generation unit configured to sequentially generate fluorescent image data in accordance with light intensity of a fluorescent wavelength component emitted from the fluorescent agent, based on the image data generated by the imaging unit each time the imaging unit generates the image data; a first calculation unit configured to sequentially calculate a change amount of the light intensity based on two sets of temporally successive fluorescent image data each time the generation unit generates the fluorescent image data; a first determination unit configured to determine whether the change amount sequentially calculated by the first calculation unit is equal to or greater than a first threshold indicating fluorescence expression; a second determination unit configured to determine whether the change amount sequentially calculated by the first calculation unit is less than a second threshold indicating a steady state of fluorescence after the first determination unit determines that the change amount is equal to or greater than the first threshold; and an output unit configured to output a message that fluorescence of the fluorescent agent is in the steady state if the second determination unit determines that the change amount is less than the second threshold.

In some embodiments, an image processing device is configured to be connected to an endoscope having an imaging unit for imaging a region of a subject to generate image data, a fluorescent agent having been administered to the subject, and the region having been irradiated with excitation light. The image processing device includes: a generation unit configured to sequentially generate fluorescent image data in accordance with light intensity of a fluorescent wavelength component emitted from the fluorescent agent, based on the image data generated by the imaging unit each time the imaging unit generates the image data; a first calculation unit configured to sequentially calculate a change amount of the light intensity based on two sets of temporally successive fluorescent image data each time the generation unit generates the fluorescent image data; a first determination unit configured to determine whether the change amount sequentially calculated by the first calculation unit is equal to or greater than a first threshold indicating fluorescence expression; a second determination unit configured to determine whether the change amount sequentially calculated by the first calculation unit is less than a second threshold indicating a steady state of fluorescence; and an output unit configured to output a message that fluorescence of the fluorescent agent is in the steady state if the second determination unit determines that the change amount is less than the second threshold after the first determination unit determines that the change amount is equal to or greater than the first threshold.

In some embodiments, an image processing method is executed by an image processing device configured to be connected to an endoscope having an imaging unit for imaging a region of a subject to generate image data, a fluorescent agent having been administered to the subject, and the region having been irradiated with excitation light. The method includes: sequentially generating fluorescent image data in accordance with light intensity of a fluorescent wavelength component emitted from the fluorescent agent, based on the image data generated by the imaging unit each time the imaging unit generates the image data; sequentially calculating a change amount of the light intensity based on two sets of temporally successive fluorescent image data each time the fluorescent image data is generated; determining whether the change amount sequentially calculated is equal to or greater than a first threshold indicating fluorescence expression; determining whether the change amount sequentially calculated is less than a second threshold indicating a steady state of fluorescence after the change amount is determined to be equal to or greater than the first threshold; and outputting a message that fluorescence of the fluorescent agent is in the steady state if the change amount is determined to be less than the second threshold.

In some embodiments, provided is a non-transitory computer-readable recording medium with an executable program stored thereon for an image processing device configured to be connected to an endoscope having an imaging unit for imaging a region of a subject to generate image data, a fluorescent agent having been administered to the subject, and the region having been irradiated with excitation light. The program causes the image processing device to execute: sequentially generating fluorescent image data in accordance with light intensity of a fluorescent wavelength component emitted from the fluorescent agent, based on the image data generated by the imaging unit each time the imaging unit generates the image data; sequentially calculating a change amount of the light intensity based on two sets of temporally successive fluorescent image data each time the fluorescent image data is generated; determining whether the change amount sequentially calculated is equal to or greater than a first threshold indicating fluorescence expression; determining whether the change amount sequentially calculated is less than a second threshold indicating a steady state of fluorescence after the change amount is determined to be equal to or greater than the first threshold; and outputting a message that fluorescence of the fluorescent agent is in the steady state if the change amount is determined to be less than the second threshold.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 3 is a diagram schematically illustrating a structure of a color filter according to the first embodiment of the present invention;

DETAILED DESCRIPTION

In the following, modes for carrying out the present invention (hereinafter referred to as "embodiments") will be described with reference to the drawings. The present invention is not limited by the embodiments described below. The same reference signs are used to designate the same elements throughout the drawings.

First Embodiment

Brief Configuration of Endoscope System

Figure 1:
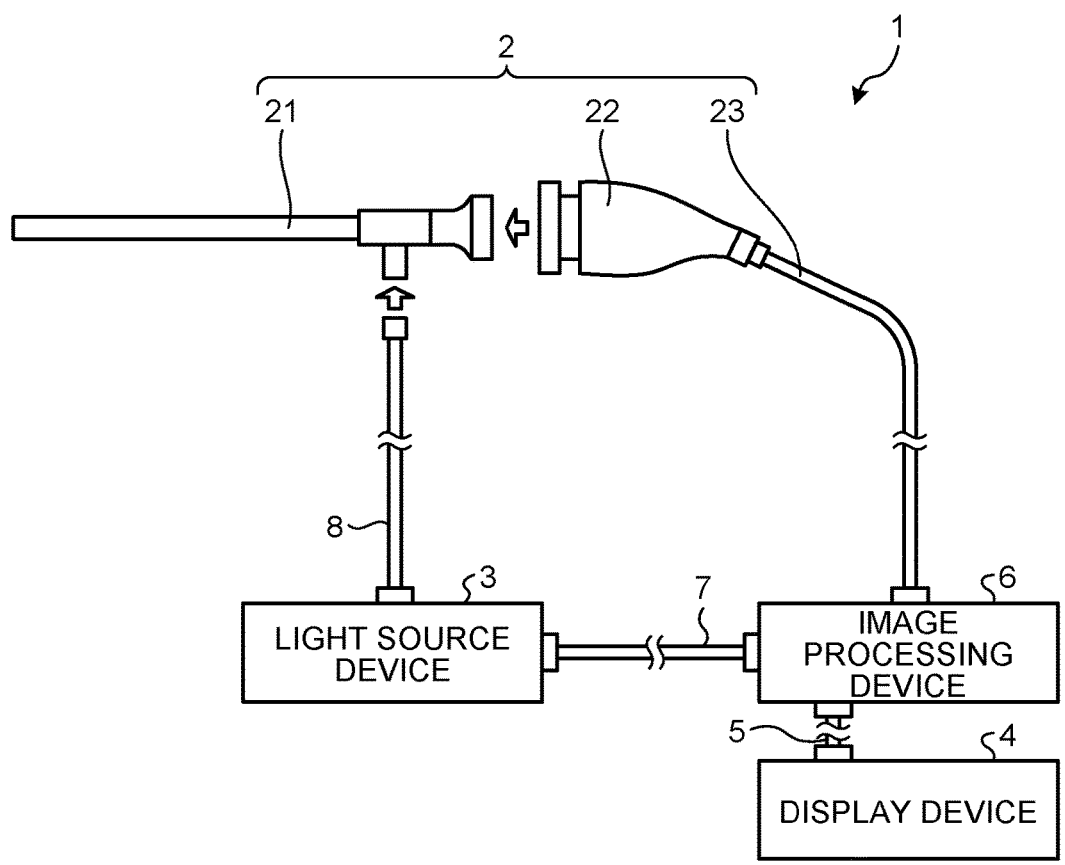
FIG. 1 is a diagram illustrating a brief structure of an endoscope system according to a first embodiment of the present invention.

FIG. 1 is a diagram illustrating a brief structure of an endoscope system according to a first embodiment of the present invention. An endoscope system 1 illustrated in FIG. 1 is a system used in the medical field and used in sentinel navigation surgery in which a site and a position of a blood vessel inside a subject is specified by: irradiating the subject with excitation light in which fluorescence is emitted by a fluorescent agent after intravenously injecting the fluorescent agent into the subject (living body) such as a human before fluorescent observation; and observing temporal change of the fluorescence while imaging the subject. In the following, note that a case of using ICG as the fluorescent agent will be described. The ICG used in the first embodiment emits fluorescence of 830 nm by excitation light of nearly 770 nm.

The endoscope system 1 illustrated in FIG. 1 includes an endoscope 2, a light source device 3, a display device 4, a second transmission cable 5, an image processing device 6 (processor), a third transmission cable 7, and a light guide 8.

The endoscope 2 images a subject in which the fluorescent agent has been administered into a living body of the subject, and outputs image data of the imaged subject. The endoscope 2 includes an inserting portion 21, a camera head 22, and a first transmission cable 23.

The inserting portion 21 is hard, has an elongated shape, and is configured to be inserted into the living body. An optical system formed by using one or more lenses and adapted to form a subject image is provided inside the inserting portion 21.

The camera head 22 is detachably connected to a proximal end of the inserting portion 21. The camera head 22 images a subject image focused at the inserting portion 21, generates image data, and outputs the same to the image processing device 6 via the first transmission cable 23 under the control of the image processing device 6. A detailed structure of the camera head 22 will be described later.

The first transmission cable 23 has one end detachably connected to the image processing device 6 and the other end connected to the camera head 22. The first transmission cable 23 transmits the image data output from the camera head 22 to the image processing device 6, and further transmits, to the camera head 22, a control signal, a synchronization signal, and a clock signal output from the image processing device 6, electric power, and the like. Meanwhile, transmission of the image data from the camera head 22 to the image processing device 6 via the first transmission cable 23 may be performed by an optical signal or may also be performed by an electric signal. Needless to say, the same is applied to transmission of the control signal, synchronization signal, and clock signal from the image processing device 6 to the camera head 22 via the first transmission cable 23.

The light source device 3 has one end of the light guide 8 connected, and supplies the one end of the light guide 8 with excitation light to excite the fluorescent agent or illumination light (such as white light) to irradiate the inside of the living body of the subject under the control of the image processing device 6. The light source device 3 is formed by using, for example, a light source such as a light emitting diode (LED) or a halogen lamp, a filter for passing a predetermined wavelength band only (e.g., approximately 770 nm).

The display device 4 displays an image corresponding to image data generated by the endoscope 2 under the control of the image processing device 6. The display device 4 is formed by using a display panel such as a liquid crystal or an organic electro luminescence (EL).

The second transmission cable 5 has one end detachably connected to the display device 4 and the other end connected to the image processing device 6. The second transmission cable 5 transmits, to the display device 4, image data after image processing by the image processing device 6. The second transmission cable 5 is formed by using, for example, an HDMI (registered trademark), a Display Port (registered trademark), or the like.

The image processing device 6 is formed by using a central processing unit (CPU) and the like, and integrally controls operation of the endoscope 2, light source device 3, and display device 4. A detailed configuration of the image processing device 6 will be described later.

The third transmission cable 7 has one end detachably connected to the light source device 3 and the other end connected to the image processing device 6. The third transmission cable 7 transmits a control signal from the image processing device 6 to the light source device 3.

The light guide 8 has one end detachably connected to the light source device 3 and the other end detachably connected to the inserting portion 21. The light guide 8 transmits, from the one end to the other end, the light supplied from the light source device 3 and supplies the same to the inserting portion 21. The light supplied to the inserting portion 21 is emitted from a distal end of the inserting portion 21 and made to irradiate the subject. The light made to irradiate the subject (subject image) is focused by the optical system inside the inserting portion 21.

Configuration of Camera Head

Figure 2:
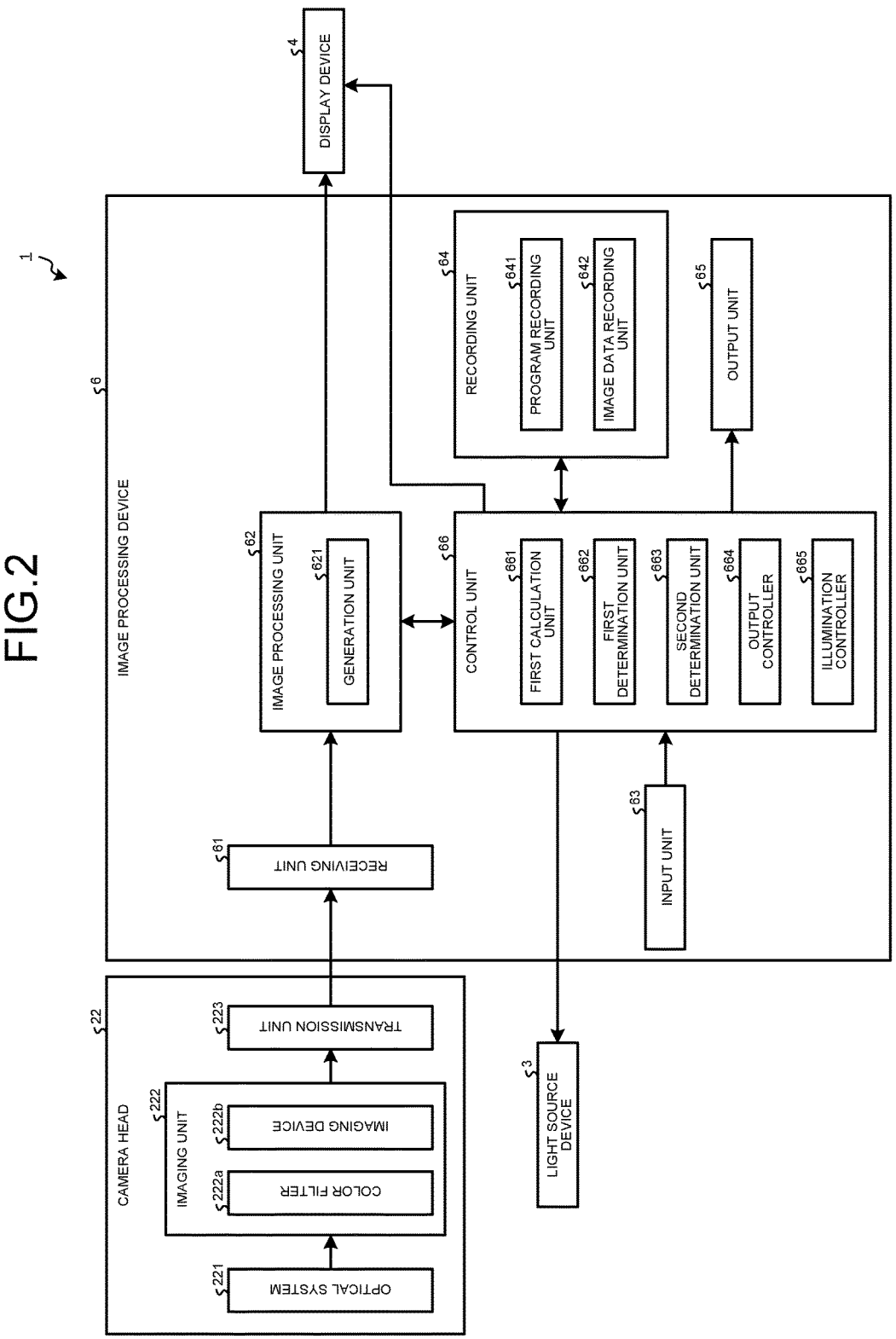
FIG. 2 is a block diagram illustrating functional configurations in a camera head of an endoscope and an image processing device according to the first embodiment of the present invention.

Next, the configuration of the camera head 22 will be described. FIG. 2 is a block diagram illustrating functional configurations in the camera head 22 and the image processing device 6.

As illustrated in FIG. 2, the camera head 22 includes an optical system 221, an imaging unit 222, and a transmission unit 223.

The optical system 221 is formed by using one or more lenses movable along an optical axis and forms, on an imaging surface of the imaging unit 222, an image of the subject image focused at the inserting portion 21. The optical system 221 is provided with an optical zoom mechanism (not illustrated) adapted to change a field angle by moving one or a plurality of lenses and a focus mechanism (not illustrated) adapted to change a focal point under the control of the image processing device 6.

The imaging unit 222 continuously images the subject and sequentially generates image data of the subject under the control of the image processing device 6. The imaging unit 222 includes a color filter 222a and an imaging device 222b.

Figure 3:
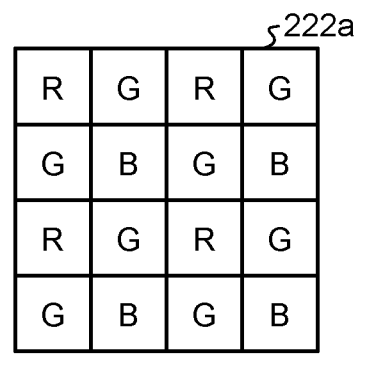

FIG. 3 is a diagram schematically illustrating a structure of the color filter 222a. The color filter 222a illustrated in FIG. 2 is formed by using a filter unit forming a predetermined array pattern (Bayer array) in which a broad band filter R adapted to pass red components, two broad band filters G adapted to pass green components, and a broad band filter B adapted to pass blue components are set as one group. The color filter 222a has sensitivity to light in a visible light range in each of light in a red wavelength band, light in a green wavelength band, and light in a blue wavelength band, and also has sensitivity to light in a near-infrared wavelength band (e.g., 830 nm). Therefore, fluorescence by the ICG can be observed.

The imaging device 222b is formed by using: an image sensor such as a charge coupled device (CCD) and a complementary metal oxide semiconductor (CMOS) adapted to photoelectrically convert light received by each of a plurality of pixels arranged in a two-dimensional lattice shape and generate an image signal; and an A/D conversion circuit adapted to generate digital image data by performing A/D conversion to an analog image signal generated by the image sensor and output the same to the image processing device 6 via the first transmission cable 23.

The transmission unit 223 transmits the image data generated by the imaging unit 222 to the image processing device 6. The transmission unit 223 is formed by using an FPGA in which a plurality of functional blocks (logic circuits) is built by reading configuration data preliminarily recorded in a non-volatile memory (not illustrated) such as an electrically erasable programmable read-only memory (EEPROM).

Configuration of Image Processing Device

Next, the configuration of the image processing device 6 will be described. The image processing device 6 includes a receiving unit 61, an image processing unit 62, an input unit 63, a recording unit 64, an output unit 65, and a control unit 66.

The receiving unit 61 receives image data transmitted from the transmission unit 223 and outputs the same to the image processing unit 62.

The image processing unit 62 performs predetermined image processing on the image data received from the receiving unit 61 and outputs the same to the display device 4. The image processing unit 62 is formed by using an FPGA, a graphics processing unit (GPU), and the like. Here, as the predetermined image processing, basic image processing including at least A/D conversion processing, optical black subtraction processing, white balance adjustment processing, synchronization processing of image data, color matrix arithmetic processing, γ correction processing, color reproduction processing, edge emphasis processing, and the like is performed. Furthermore, the image processing unit 62 includes a generation unit 621.

Each time the imaging unit 222 generates image data, the generation unit 621 sequentially generates fluorescent image data in accordance with light intensity in a wavelength band of fluorescence emitted from the fluorescent agent based on the image data, and transmits the fluorescent image data to the control unit 66 and the display device 4. Here, the fluorescent image data is image data in which a signal value (pixel value or luminance information) in accordance with the light intensity of a fluorescent wavelength component emitted from the fluorescent agent is recorded per pixel.

The input unit 63 is formed by using a switch, a button, and the like, and adapted to receive input of command signals that provide commands for various kinds of operation related to the endoscope system 1, and outputs the received command signals to the control unit 66.

The recording unit 64 is formed by using a read only memory (ROM), a random access memory (RAM), a flash memory, and the like and records various kinds of programs executed by the endoscope system 1, data under processing, image data, and fluorescent image data. The recording unit 64 includes: a program recording unit 641 adapted to record the programs executed by the endoscope system 1; and an image data recording unit 642 adapted to record the image data and fluorescent image data.

The output unit 65 outputs, under the control of the control unit 66, a message that the fluorescent agent administered to the subject is in a steady state. The output unit 65 is formed by using: a speaker adapted to output sound; a display panel such as a liquid crystal and an organic EL capable of displaying characters; an LED lamp and the like which can be turned on or blinked and emits light to the outside.

The control unit 66 is formed by using a CPU and the like, and integrally controls operation of the respective units constituting the endoscope system 1. The control unit 66 includes a first calculation unit 661, a first determination unit 662, a second determination unit 663, and an output controller 664, and an illumination controller 665.

Each time the generation unit 621 generates fluorescent image data, the first calculation unit 661 calculates, based on two temporally successive fluorescent image data, a change amount of fluorescent image data of a current frame (hereinafter referred to as "second fluorescent image") from fluorescent image data of a previous frame (hereinafter referred to as "first fluorescent image") while setting, as an index, the light intensity of the fluorescent wavelength component. Specifically, based on the two temporally successive fluorescent image data, the first calculation unit 661 calculates, per pixel, a difference of signal value of the second fluorescent image from the first fluorescent image while setting the light intensity of the fluorescent wavelength component as the index, and calculates, as a change amount, a sum of the calculated differences of the signal values in the respective pixels.

The first determination unit 662 determines whether the change amount calculated by the first calculation unit 661 is equal to or greater than a first threshold indicating fluorescence expression. Here, the first threshold is a value when fluorescence is emitted with predetermined intensity if excitation light is emitted to the subject to which the fluorescent agent has been preliminarily administered.

After the first determination unit 662 determines that the change amount calculated by the first calculation unit 661 is the first threshold or more, the second determination unit 663 determines whether the change amount calculated by the first calculation unit 661 is less than a second threshold indicating that fluorescence is in the steady state.

If the second determination unit 663 determines that the change amount calculated by the first calculation unit 661 is less than the second threshold after the first determination unit 662 determines that the change amount calculated by the first calculation unit 661 is the first threshold or more, the output controller 664 causes the output unit 65 to output the message that fluorescence of the fluorescent agent is in the steady state or causes the display device 4 to display the message. The output controller 664 controls a display style of the display device 4. Specifically, the output controller 664 causes the display device 4 to display various kinds of information related to the endoscope system 1. Also, the output controller 664 causes the display device 4 to display an image corresponding to image data obtained by image processing by the image processing unit 62.

The illumination controller 665 controls the light source device 3. Specifically, the illumination controller 665 switches a kind of light to be emitted by the light source device 3 to white light or to excitation light and causes the light source device 3 to emit the light.

Temporal Change of Fluorescent Image

Figure 4:
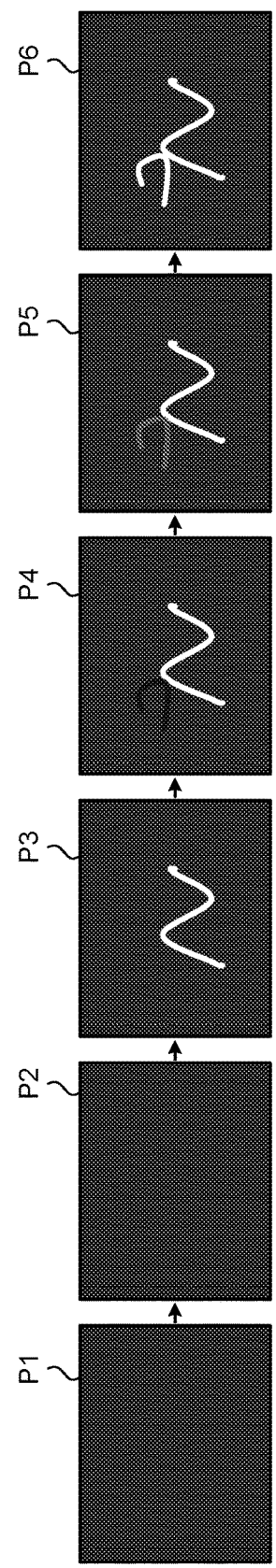
FIG. 4 is a diagram illustrating exemplary temporal change of a fluorescent image generated by an imaging unit according to the first embodiment of the present invention.
Figure 5:
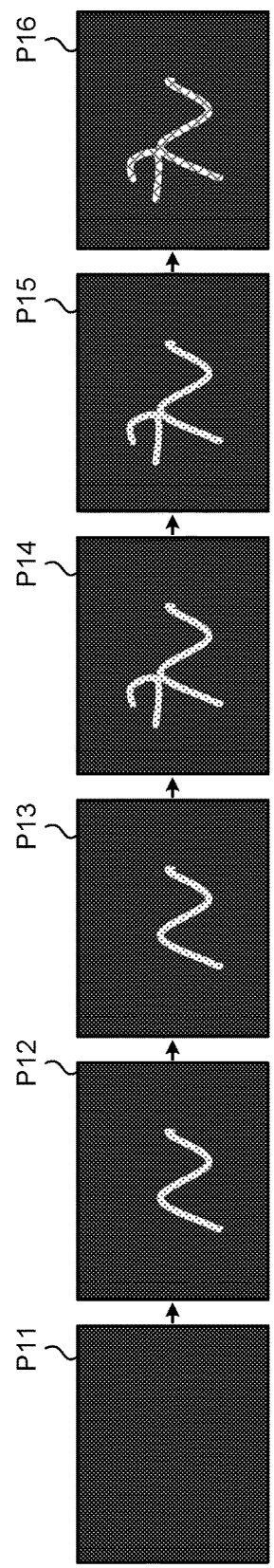
FIG. 5 is a diagram illustrating exemplary temporal change of a difference image obtained by calculating a difference of a pixel value every predetermined period from time series data in the fluorescent image generated by the imaging unit according to the first embodiment of the present invention.

Next, temporal change of a fluorescent image generated by the imaging unit 222 will be described. FIG. 4 is a diagram illustrating exemplary temporal change of the fluorescent image generated by the imaging unit 222. FIG. 5 is a diagram illustrating exemplary temporal change of a difference image obtained by calculating a difference of a pixel value every predetermined period from time series data in the fluorescent image generated by the imaging unit 222.

As illustrated in FIG. 4, as the time passes, the ICG that is the fluorescent agent reaches a blood vessel and a lymph node after intravenous injection, and the fluorescent image emits fluorescence (fluorescent image P1→fluorescent image P2→fluorescent image P3→fluorescent image P4→fluorescent image P5→fluorescent image P6). Furthermore, since the fluorescence by the ICG is extremely weak as illustrated in FIG. 4, it is difficult to visually determine the time when fluorescence is expressed and the fact that the fluorescence is in the steady state.

As illustrated in FIG. 5, fluorescence of the ICG can be more easily observed in the difference image compared to the fluorescent image (difference image P11→difference image P12→difference image P13→difference image P14→difference image P15→difference image P16), but it is difficult to visually determine the fact that the fluorescence is in the steady state.

Figure 6:
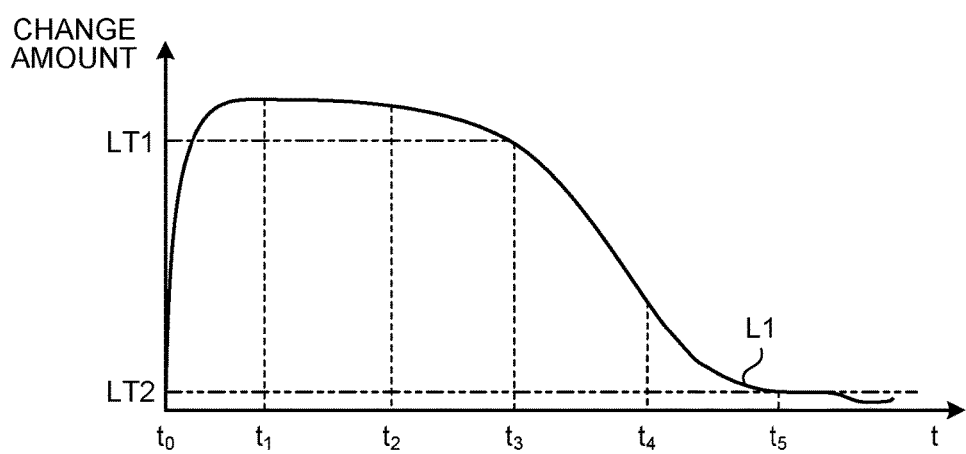
FIG. 6 is a diagram illustrating a relation between time and change of a change amount calculated by a first calculation unit according to the first embodiment of the present invention.

FIG. 6 is a diagram illustrating a relation between time and change of the change amount calculated by the first calculation unit 661. In FIG. 6, a horizontal axis represents time, and a vertical axis represents the change amount. In FIG. 6, a curve L1 represents the change amount calculated by the first calculation unit 661.

As indicated by the curve L1 in FIG. 6, change amount once rapidly rise and then the change amount gradually decreases with time passage. Therefore, in the first embodiment, as illustrated in FIG. 6, each time the fluorescent image data is generated by the generation unit 621, the first calculation unit 661 sequentially calculates, based on the two temporally successive fluorescent image data, a change amount of light intensity of the second fluorescent image from the first fluorescent image while setting the light intensity of the fluorescent wavelength component as the index, and if the change amount calculated by the first calculation unit 661 becomes less than the second threshold LT2 indicating the steady state of fluorescence after the change amount calculated by the first calculation unit 661 becomes the first threshold LT1 indicating fluorescence expression, it is determined that change of the fluorescent image becomes little and the fluorescence is in the steady state, and the fact that the fluorescence is in the steady state is output to a user. Consequently, the user such as a doctor can easily grasp the fact that the fluorescence of the fluorescent agent is in the steady state. As a result, it is possible to assist a doctor in determining whether light emission of the fluorescent agent is in the steady state.

Processing of Endoscope System

Figure 7:
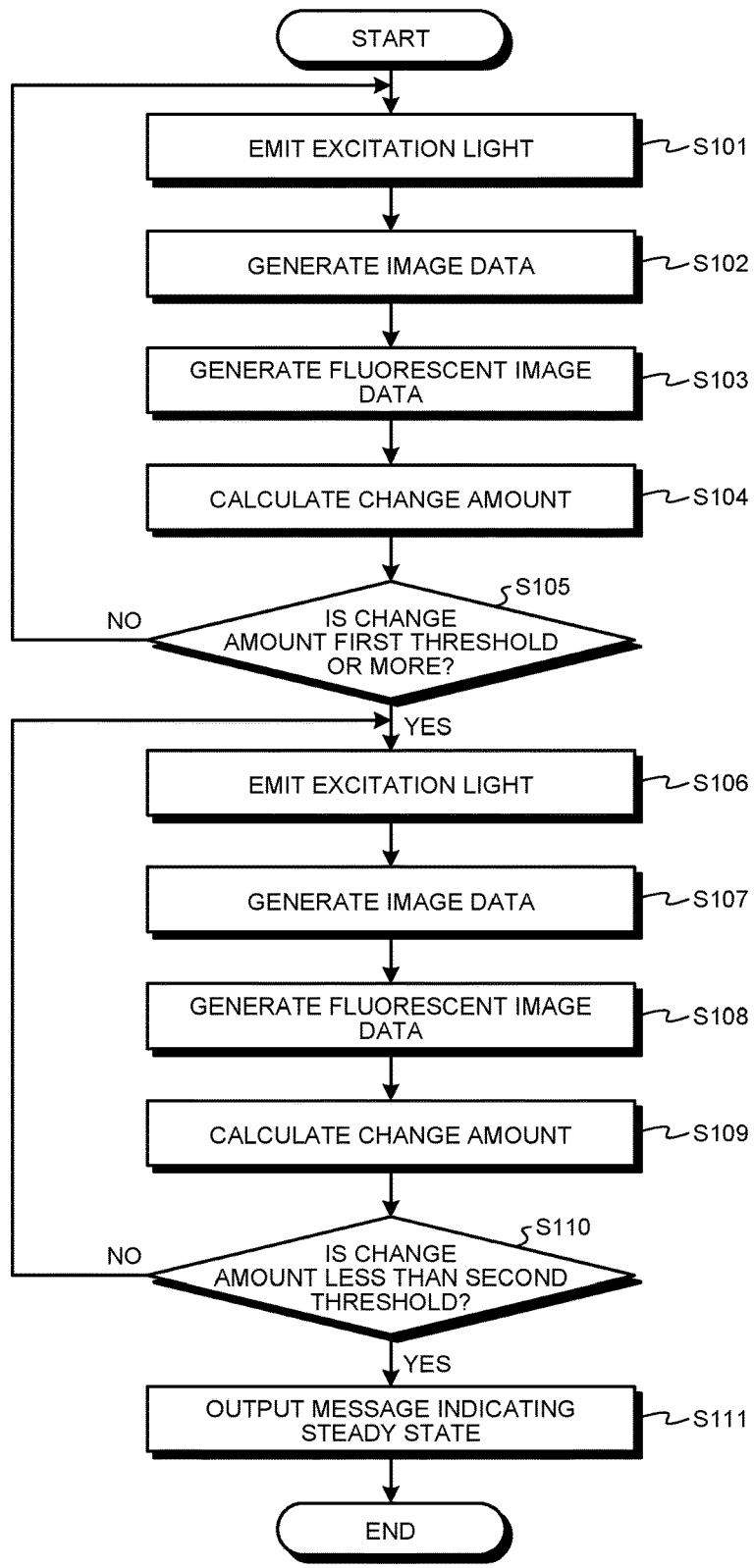
FIG. 7 is a flowchart illustrating an outline of processing executed by an endoscope system according to the first embodiment of the present invention.

Next, processing executed by the endoscope system 1 will be described. FIG. 7 is a flowchart illustrating an outline of the processing executed by the endoscope system 1.

As illustrated in FIG. 7, the light source device 3 first emits excitation light to a subject to which a fluorescent agent has been administered (Step S101).

Subsequently, the imaging unit 222 images the subject to which the light source device 3 emits the excitation light, and generates image data (Step S102).

After that, the generation unit 621 generates, based on the image data generated by the imaging unit 222, fluorescent image data in which a pixel value in accordance with light intensity of a fluorescent wavelength component emitted from the fluorescent agent is correlated to each pixel (Step S103).

Figure 8A:
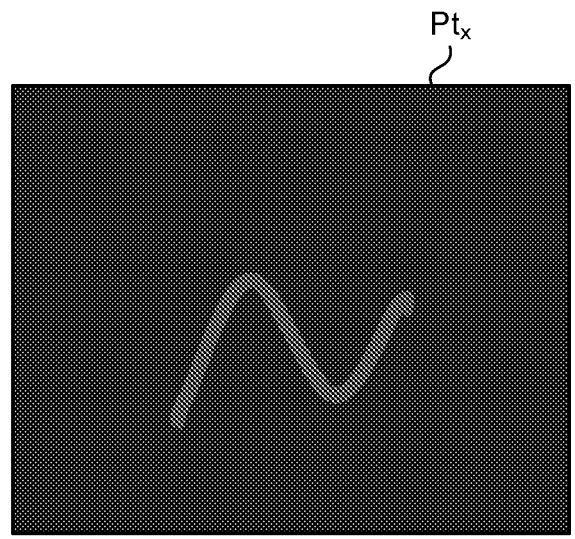
FIG. 8A is a diagram illustrating an exemplary fluorescent image of a current frame according to the first embodiment of the present invention.
Figure 8B:
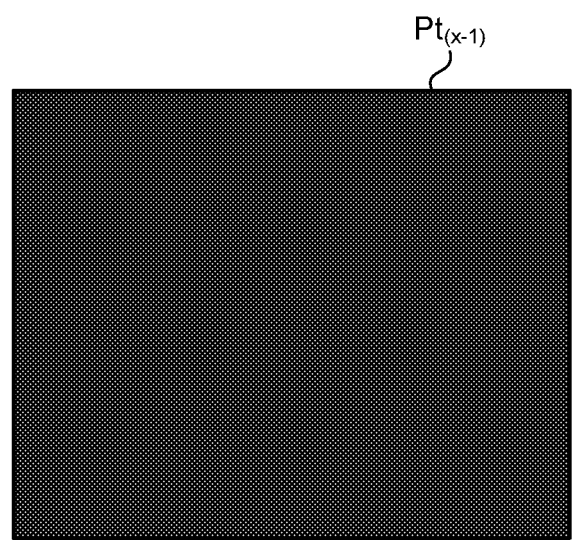
FIG. 8B is a diagram illustrating an exemplary fluorescent image of a previous frame according to the first embodiment of the present invention.
Figure 8C:
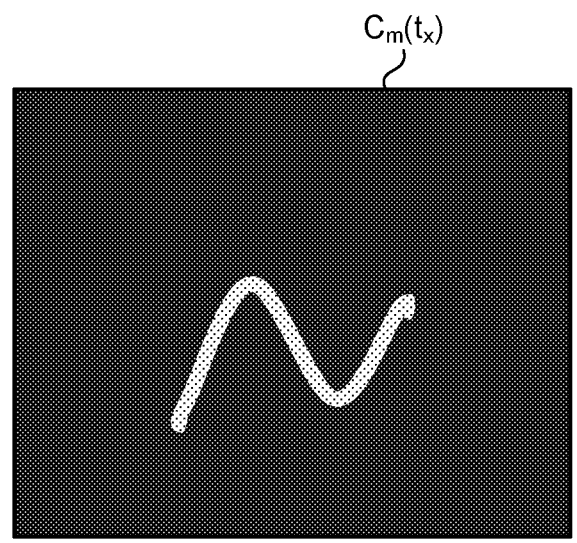
FIG. 8C is a diagram illustrating an exemplary difference image according to the first embodiment of the present invention.

Subsequently, the first calculation unit 661 calculates a change amount of the light intensity of the fluorescent wavelength component based on two temporally successive fluorescent image data generated by the generation unit 621 (Step S104). Specifically, as illustrated in FIGS. 8A to 8C, the first calculation unit 661 calculates the change amount by a following Formula (1) when a signal value of each pixel is defined as $I_m(t_x)$ in a fluorescent image $Pt_x$ of a current frame at the time of $t=t_x$.

$$\sum_m C_m(t_x) = \sum_m (I_m(t_x) - I_m(t_{x-1})) \qquad (1)$$

Here, m represents a pixel address (coordinate), $I_m(t_{x-1})$ represents a signal value of each pixel in a fluorescent image $Pt_{(x-1)}$ of a previous frame generated more previous than the fluorescent image $Pt_x$ of the current frame.

Thus, the first calculation unit 661 compares, per pixel, the signal value $I_m(t_{x-1})$ in the fluorescent image $Pt_{x-1}$ of the previous frame with the signal value $I_m(t_x)$ in the fluorescent image $Pt_x$ of the current frame generated by the generation unit 621, and calculates a sum of the differences of the signal values in the respective pixels as the change amount of the light intensity of the second fluorescent image from the first fluorescent image while setting the light intensity of the fluorescent wavelength component as the index.

Referring back to FIG. 7, processing from Step S105 will be described.

In Step S105, the first determination unit 662 determines whether the change amount calculated by the first calculation unit 661 is the first threshold or more. If the first determination unit 662 determines that the change amount calculated by the first calculation unit 661 is the first threshold or more (Step S105: Yes), the endoscope system 1 proceeds to Step S106 described later. In contrast, if the first determination unit 662 determines that the change amount calculated by the first calculation unit 661 is not the first threshold or more (Step S105: No), the endoscope system 1 returns to Step S101 described above.

In Step S106, the light source device 3 emits excitation light to the subject to which the fluorescent agent has been administered.

Subsequently, the imaging unit 222 images the subject to which the light source device 3 emits the excitation light, and generates image data (Step S107).

After that, the generation unit 621 generates, based on the image data generated by the imaging unit 222, fluorescent image data in which the pixel value in accordance with the light intensity of the fluorescent wavelength component emitted from the fluorescent agent is correlated to each pixel (Step S108).

Subsequently, the first calculation unit 661 calculates a change amount of the light intensity of the fluorescent wavelength component based on two temporally successive fluorescent image data generated by the generation unit 621 (Step S109).

Then, the second determination unit 663 determines whether the change amount calculated by the first calculation unit 661 is less than the second threshold (Step S110). If the second determination unit 663 determines that the change amount calculated by the first calculation unit 661 is less than the second threshold (Step S110: Yes), the endoscope system 1 proceeds to Step S111 described later. In contrast, if the second determination unit 663 determines that the change amount calculated by the first calculation unit 661 is not less than the second threshold (Step S110: No), the endoscope system 1 returns to Step S106 described above.

In Step S111, the output unit 65 outputs the message that fluorescence of the fluorescent agent has become steady state. Specifically, the output controller 664 causes the output unit 65 to output the message that the fluorescence of the fluorescent agent is in the steady state by using sound, alarm, and the like. Consequently, the user can easily grasp that the fluorescence of the fluorescent agent is in the steady state.

According to the first embodiment of the present invention, if the change amount calculated by the first calculation unit 661 is less than the second threshold after the change amount calculated by the first calculation unit 661 has become the first threshold or more, the user can easily grasp that the fluorescence of the fluorescent agent is in the steady state because the output unit 65 outputs the message that the fluorescence of the fluorescent agent is in the steady state unit.

First Modified Example of First Embodiment

Next, a first modified example of the first embodiment of the present invention will be described. According to the first embodiment, the first calculation unit 661 calculates, per pixel, a difference of fluorescent image data of the current frame from fluorescent image data of the previous frame while setting, as the index, the light intensity of the fluorescent wavelength component based on the two temporally successive fluorescent image data generated by the generation unit 621, and calculates the sum of the differences as the change amount. However, in the first modified example of the first embodiment, division is made into a plurality of blocks each having predetermined pixels, a difference of fluorescent image data of a current frame from fluorescent image data of previous frame is calculated while setting, as an index, light intensity of a fluorescent wavelength component of each of the divided plurality of blocks, and a sum of the differences is calculated as a change amount. In the following, a calculation method performed by the first calculation unit 661 according to the first modified example of the first embodiment will be described.

Figure 9A:
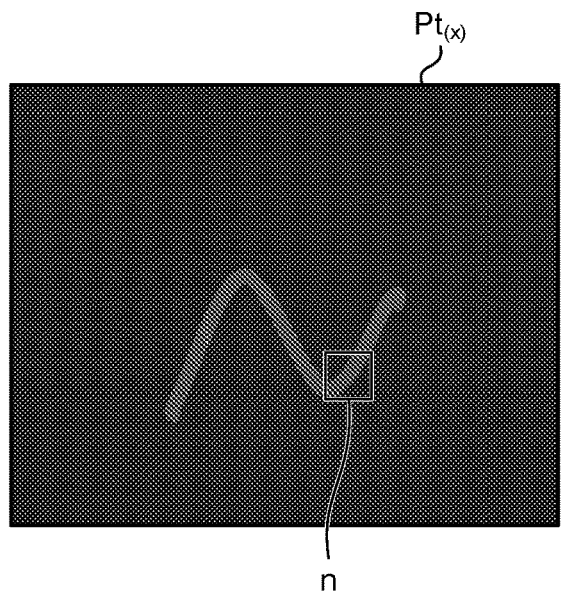
FIG. 9A is a diagram illustrating an exemplary fluorescent image of a current frame according to a first modified example of the first embodiment of the present invention.
Figure 9B:
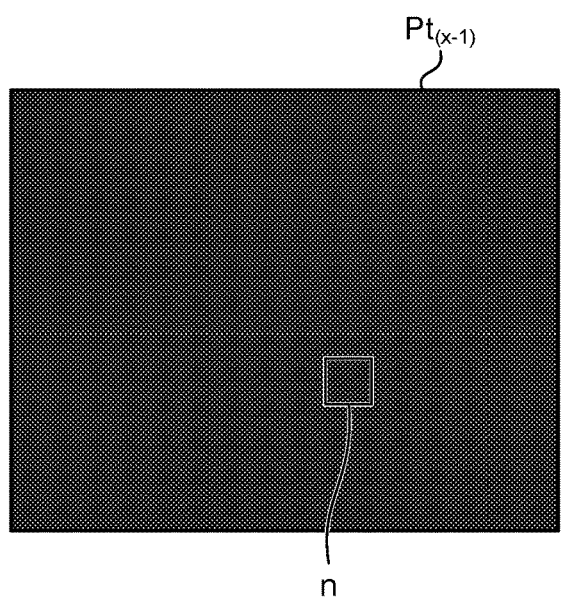
FIG. 9B is a diagram illustrating an exemplary fluorescent image of a previous frame according to the first modified example of the first embodiment of the present invention.
Figure 9C:
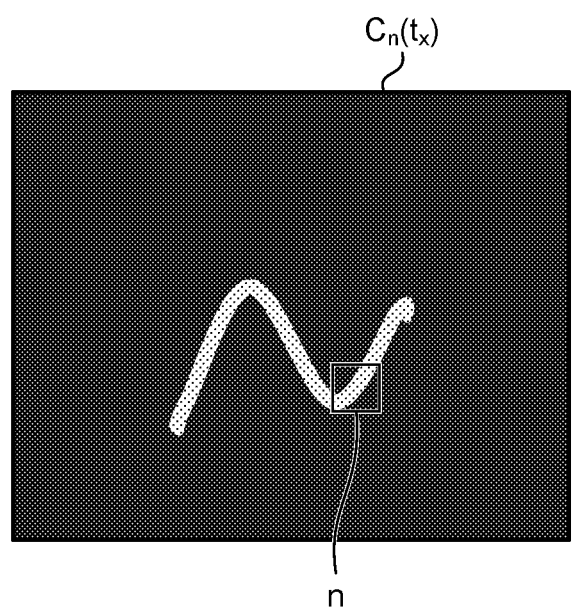
FIG. 9C is a diagram illustrating an exemplary difference image according to the first modified example of the first embodiment of the present invention.

FIG. 9A is a diagram illustrating an exemplary fluorescent image of a current frame. FIG. 9B is a diagram illustrating an exemplary fluorescent image of a previous frame. FIG. 9C is a diagram illustrating an exemplary difference image. In FIGS. 9A and 9B, a region n represents a block having the specified number of pixels.

As illustrated in FIGS. 9A to 9C, the first calculation unit 661 divides the fluorescent image corresponding to fluorescent image data into the plurality of blocks each having the specified number of pixels, calculates a difference of the fluorescent image data of the current frame from fluorescent image data of the previous frame while setting, as an index, light intensity of a fluorescent wavelength component in each of the divided plurality of blocks, and calculates the sum of the differences as the change amount. Specifically, the first calculation unit 661 calculates the change amount by a following Formula (2) when a signal value of the block n (region n) is defined as $I_n(t_x)$ in a fluorescent image $Pt_x$ of the current frame at the time of $t=t_x$.

$$\sum_n C_n(t_x) = \sum_n (I_n(t_x) - I_n(t_{x-1})) \quad (2)$$

Here, $I_n(t_{x-1})$ represents a signal value obtained by averaging signal values of the pixels in the block n in a fluorescent image $Pt_{(x-1)}$ of the previous frame generated more previous than the fluorescent image $Pt_x$ of the current frame.

Thus, the first calculation unit 661 compares, for each block n, the signal value $I_n(t_{x-1})$ in the fluorescent image $Pt_{x-1}$ of the previous frame with the signal value $I_n(t_x)$ in the fluorescent image $Pt_x$ of the current frame generated by the generation unit 621, and calculates the sum of differences of the respective blocks as the change amount of the second fluorescent image from the first fluorescent image while setting, as the index, the light intensity of the fluorescent wavelength component.

According to the first modified example of the first embodiment, the first calculation unit 661 compares the signal value of the fluorescent image of previous frame with the signal value of the fluorescent image of the current frame generated by the generation unit 621, and calculates the difference of the fluorescent image data of the current frame from the fluorescent image data of the previous frame for each block while setting the light intensity of the fluorescent wavelength component as the index, and then calculates the sum of the differences as the change amount. Therefore, influence of noise generated in a pixel can be reduced.

Second Embodiment

Next, a second embodiment of the present invention will be described. An endoscope system according to the second embodiment is different in a configuration of the image processing device 6 according to the first embodiment and further different in processing executed by the endoscope system. Specifically, in the second embodiment, if there is no change in a change amount, a time interval between a first fluorescent image and a second fluorescent image used when a first calculation unit performs calculation is changed. In the following, a configuration of the endoscope system according to the second embodiment will be described first, and then the processing executed by the endoscope system according to the second embodiment will be described. The same elements as those of the endoscope system 1 according to the first embodiment will be denoted by the same reference signs, and the explanation thereof will be omitted.

Configuration of Endoscope System

Figure 10:
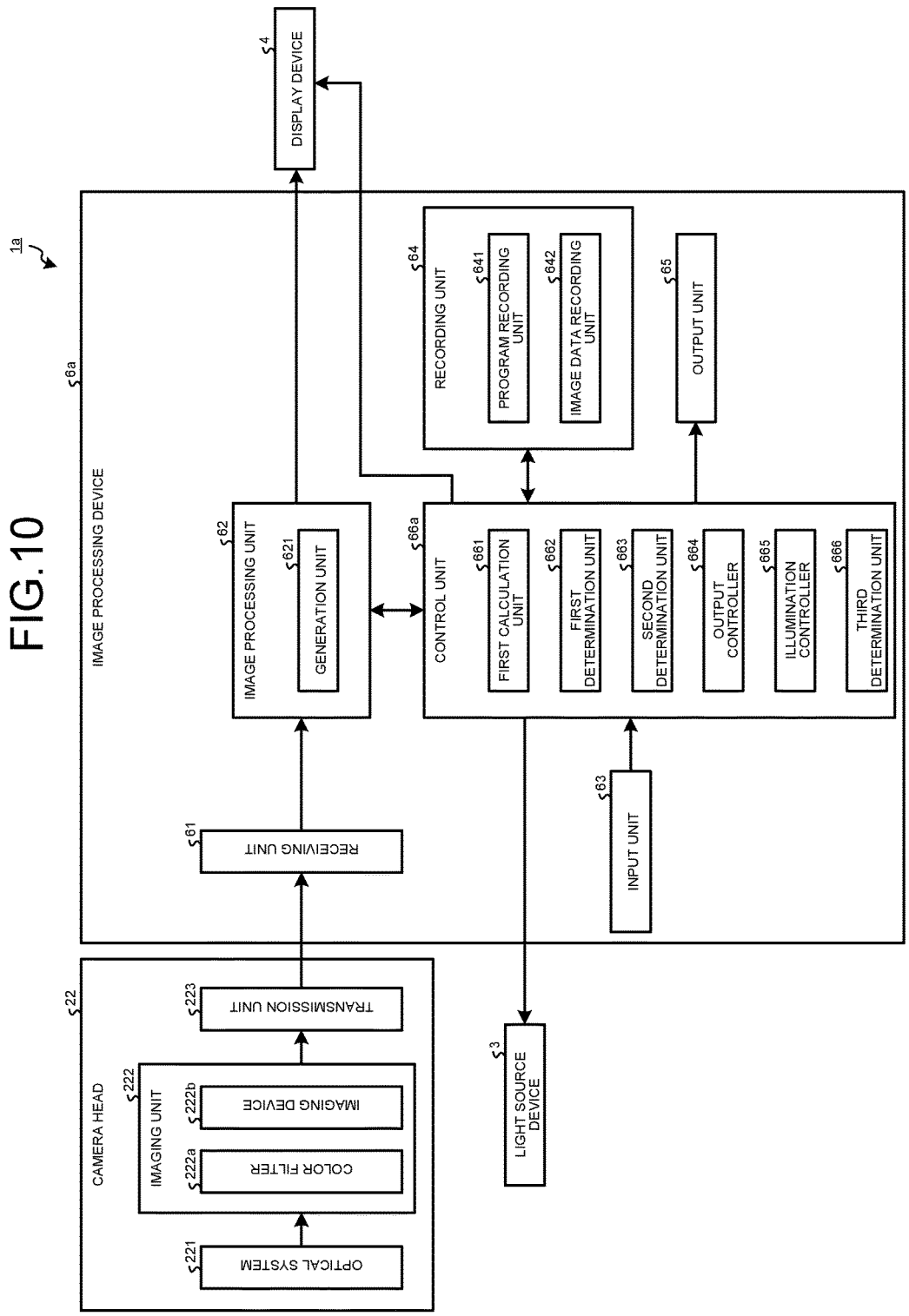
FIG. 10 is a block diagram illustrating a functional configuration of an endoscope system according to a second embodiment of the present invention.

FIG. 10 is a block diagram illustrating a functional configuration of the endoscope system according to the second embodiment of the present invention. An endoscope system 1a illustrated in FIG. 10 includes an image processing device 6a instead of the image processing device 6 according to the first embodiment. The image processing device 6a includes a control unit 66a instead of a control unit 66 according to the first embodiment. The control unit 66a further includes a third determination unit 666 in addition to a configuration of the control unit 66 according to the first embodiment.

The third determination unit 666 determines whether a change amount calculated by a first calculation unit 661 is a third threshold or more. Here, the third threshold is a value by which noise generated at an imaging device 222b can be distinguished from light emission of fluorescence, and also is a value preset by a test and the like.

Processing of Endoscope System

Figure 11:
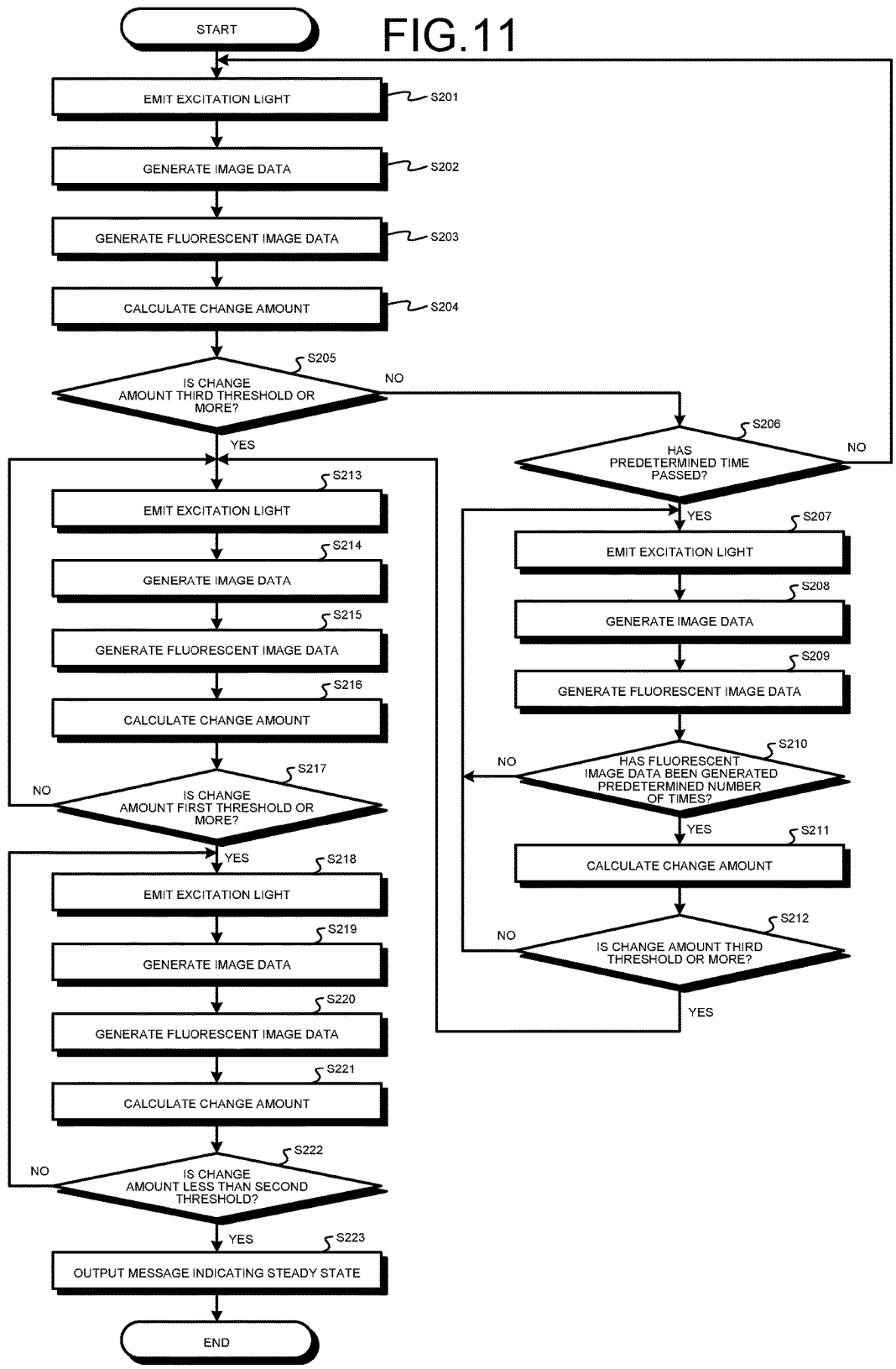
FIG. 11 is a flowchart illustrating an outline of processing executed by the endoscope system according to the second embodiment of the present invention.

Next, processing executed by the endoscope system 1a will be described. FIG. 11 is a flowchart illustrating an outline of the processing executed by the endoscope system 1a.

In FIG. 11, Steps S201 to S204 correspond to above-described Steps S101 to Step S104 in FIG. 7 respectively.

In Step S205, the third determination unit 666 determines whether the change amount calculated by the first calculation unit 661 is the third threshold or more. If the third determination unit 666 determines that the change amount calculated by the first calculation unit 661 is the third threshold or more (Step S205: Yes), the endoscope system 1a proceeds to Step S213 described later. In contrast, if the third determination unit 666 determines that the change amount calculated by the first calculation unit 661 is not the third threshold or more (Step S205: No), the endoscope system 1a proceeds to Step S206 described later.

Figure 12:
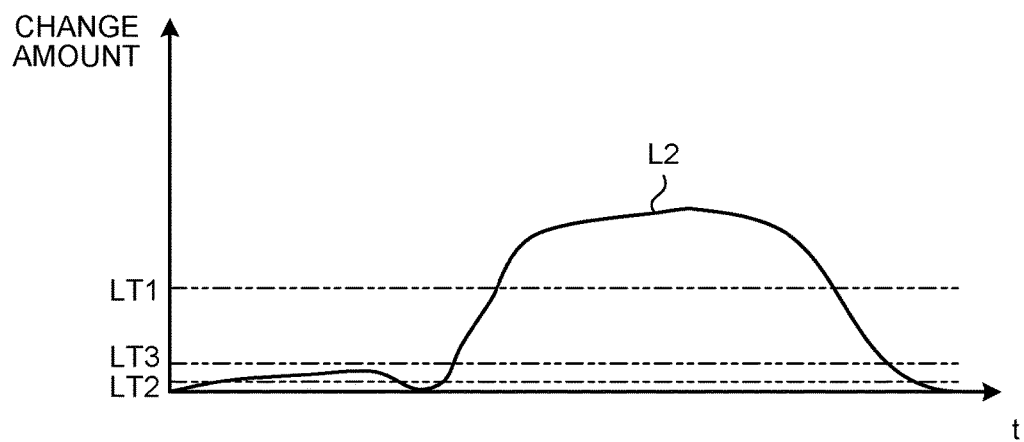
FIG. 12 is a diagram schematically illustrating exemplary temporal change of a change amount calculated by a first calculation unit according to the second embodiment of the present invention.

FIG. 12 is a diagram schematically illustrating exemplary temporal change of the change amount calculated by the first calculation unit 661. In FIG. 12, a horizontal axis represents time, and a vertical axis represents the change amount. In FIG. 12, a curve L2 represents temporal change of the change amount calculated by the first calculation unit 661.

As illustrated in FIG. 12, since fluorescence of a fluorescent agent is weak, a change amount of a signal value of a second fluorescent image from a signal amount of a first fluorescent image calculated by the first calculation unit 661 while setting, as an index, light intensity of a fluorescent wavelength component may become extremely little, and it may be difficult to distinguish noise from the signal value by the fluorescence. Therefore, in the second embodiment, if the third determination unit 666 determines that the change amount calculated by the first calculation unit 661 is not equal to or greater than the third threshold LT3 indicating noise, a time interval between the temporally successive first fluorescent image and second fluorescent image calculated by the first calculation unit 661 is increased. In other words, if the generation unit 621 generates fluorescent image data predetermined number of times, for example, generates the fluorescent image data three times, the first calculation unit 661 calculates a change amount of light intensity while setting the fluorescent image data initially generated (oldest fluorescent image data) as the first fluorescent image and setting the fluorescent image data generated last (latest fluorescent image data) as the second fluorescent image.

Referring back to FIG. 11, processing from Step S206 will be described.

In Step S206, if predetermined time has passed, for example, the time to start light emission from a fluorescent agent has passed after a subject is irradiated with excitation light (Step S206: Yes), the endoscope system 1a proceeds to Step S207 described later. In contrast, if the predetermined time has not passed (Step S206: No), the endoscope system 1a returns to Step S201 described above.

In Step S207, the light source device 3 emits excitation light to the subject to which the fluorescent agent has been administered.

Subsequently, the imaging unit 222 images the subject irradiated with the excitation light by the light source device 3, and generates image data (Step S208).

After that, the generation unit 621 generates, based on the image data generated by the imaging unit 222, fluorescent image data in which a pixel value in accordance with light intensity of the fluorescent wavelength component emitted from the fluorescent agent is correlated to each pixel (Step S209).

Subsequently, if the generation unit 621 generates the fluorescent image data the predetermined number of times (Step S210: Yes), the endoscope system 1a proceeds to Step S211 described later. In contrast, if the generation unit 621 does not generate the fluorescent image data the predetermined number of times (Step S210: No), the endoscope system 1a returns to Step S207 described above.

In Step S211, the first calculation unit 661 calculates a change amount of light intensity while setting the fluorescent image data initially generated (oldest fluorescent image data) by the generation unit 621 as the first fluorescent image and setting the fluorescent image data generated last (latest fluorescent image data) as the second fluorescent image. Specifically, the first calculation unit 661 calculates the change amount by a following Formula (3) when a signal value of each pixel is defined as $I_m(t_{x+1})$ in a fluorescent image of a current frame at the time of $t=t_{x+1}$.

$$\sum_m C_m(t_{x+1}) = \sum_m (I_m(t_{x+1}) - I_m(t_{x-1})) \quad (3)$$

Here, m represents a pixel address (coordinate), $I_m(t_{x-1})$ represents a signal value of each pixel in a fluorescent image of a previous frame generated more previous than the fluorescent image of the current frame.

Subsequently, the third determination unit 666 determines whether the change amount calculated by the first calculation unit 661 is the third threshold or more. If the third determination unit 666 determines that the change amount calculated by the first calculation unit 661 is the third threshold or more (Step S212: Yes), the endoscope system 1a proceeds to Step S213 described later. In contrast, if the third determination unit 666 determines that the change amount calculated by the first calculation unit 661 is not the third threshold or more (Step S212: No), the endoscope system 1a returns to Step S207 described above.

Steps S213 to S222 correspond to above-described Steps S101 to S110 in FIG. 7 respectively.

According to the second embodiment, if the third determination unit 666 determines that the change amount calculated by the first calculation unit 661 is not the third threshold or more, the change amount of the light intensity is calculated by increasing the time interval between the temporally successive first fluorescent image and second fluorescent image calculated by the first calculation unit 661, and the change amount can be stably calculated even when there is little change of fluorescence. Therefore, even when fluorescence of the fluorescent agent is weak, it is possible to surely notify a user of a steady state.

In the second embodiment, if the third determination unit 666 determines that the change amount calculated by the first calculation unit 661 is not the third threshold or more, the change amount of the light intensity is calculated by increasing the time interval between the temporally successive first fluorescent image and second fluorescent image calculated by the first calculation unit 661. However, the change amount may also be calculated by using fluorescent image data sequentially recorded in a recording unit 64, for example. Specifically, if the third determination unit 666 determines that the change amount calculated by the first calculation unit 661 is not the third threshold or more, the first calculation unit 661 may also calculate the change amount of the light intensity between the temporally successive fluorescent image data of the previous frame and fluorescent image data of the current frame based on the oldest fluorescent image data recorded in the recording unit 64 and fluorescent image data generated by the generation unit 621 after passage of a predetermined time (e.g., after 60 seconds). Needless tom mention, if the third determination unit 666 determines that the change amount calculated by the first calculation unit 661 is not the third threshold or more, the first calculation unit 661 may re-calculate the change amount by increasing the time interval so as to reduce the number of times of calculating the change amount relative to a group of fluorescent image data sequentially recorded in the recording unit 64 in time series.

First Modified Example of Second Embodiment

Next, a first modified example of the second embodiment of the present invention will be described. In the first embodiment, if the third determination unit 666 determines that the change amount is not the third threshold or more, the change amount is calculated by increasing the time interval between the temporally successive first fluorescent image and second fluorescent image calculated by the first calculation unit 661 while setting light intensity of the fluorescent wavelength component as the index. However, according to the first modified example of the second embodiment, if the third determination unit 666 determines that the change amount is not the third threshold or more, the difference of the second fluorescent image from the first fluorescent image while setting the light intensity of the fluorescent wavelength component as the index is calculated by increasing number of pixels included in blocks each having specified number of pixels, and a sum of the differences is calculated as the change amount. In the following, a calculation method calculated by the first calculation unit 661 according to the first modified example of the second embodiment will be described.

Figure 13:
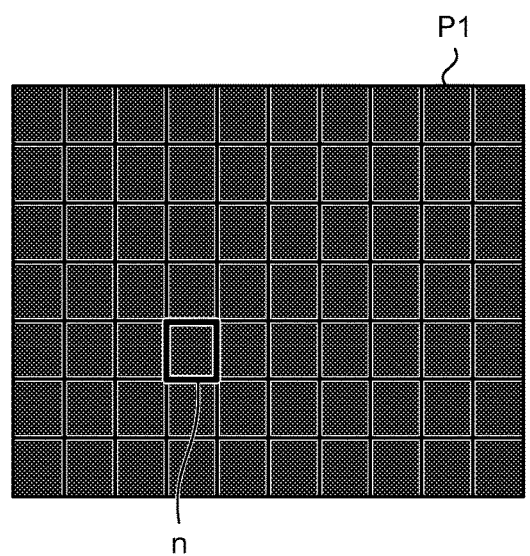
FIG. 13 is a diagram schematically describing an exemplary block for which a first calculation unit according to a first modified example of the second embodiment of the present invention calculates a change amount.
Figure 14:
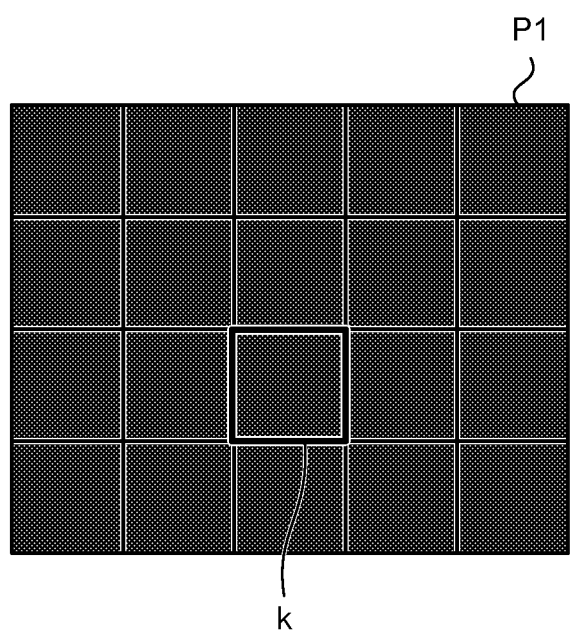
FIG. 14 is a diagram schematically describing an exemplary block for which the first calculation unit calculates a change amount if a third determination unit according to the first modified example of the second embodiment of the present invention determines that a change amount is not a third threshold or more.

FIG. 13 is a diagram schematically describing an exemplary block for which the first calculation unit 661 calculates a change amount. FIG. 14 is a diagram schematically describing an exemplary block for which the first calculation unit 661 calculates the change amount if the third determination unit 666 determines that the change amount is not the third threshold or more. In FIG. 13, a block n (region n) represents a block having a specified number of pixels. In FIG. 14, a block k represents a block where the pixels are more increased from the number of pixels in the block n. In other words, if the third determination unit 666 determines that the change amount is not the third threshold or more, the first calculation unit 661 generates, in a fluorescent image P1, a plurality blocks k by the blocks k each having the number of pixels more increased from the number of pixels in the block n. Consequently, the number of blocks k becomes fewer than the number of blocks n.

As illustrated in FIGS. 13 and 14, if the third determination unit 666 determines that the change amount is not the third threshold or more, the first calculation unit 661 calculates the change amount by a following Formula (4) when a signal value of the block k (region k) in a fluorescent image $Pt_x$ of a current frame is defined as $I_k(t_x)$ at the time of $t=t_x$.

$$\sum_k C_k(t_k) = \sum_k (I_k(t_k) - I_k(t_{x-1})) \qquad (4)$$

Here, $I_k(t_{x-1})$ represents a signal value obtained by averaging signal values of pixels in the block k in a fluorescent image $Pt_{x-1}$ of a previous frame generated more previous than the fluorescent image $Pt_x$ of the current frame.

Thus, if the third determination unit 666 determines the change amount is not the third threshold or more, the first calculation unit 661 calculates the change amount of the second fluorescent image from the first fluorescent image while setting the light intensity of the fluorescent wavelength component as the index by increasing the number of pixels included in the block (enlarging a region for which the change amount is calculated).

According to the first modified example of the second embodiment, when the third determination unit 666 determines that the change amount is not the third threshold or more, the change amount of the second fluorescent image from the first fluorescent image while setting the light intensity of the fluorescent wavelength component as the index is calculated by increasing the number of pixels included in the block. Consequently, even when there is little change of the fluorescence, it is possible to surely notify a user of the steady state.

Third Embodiment

Next, a third embodiment of the present invention will be described. An endoscope system according to a third embodiment is different in a configuration of an endoscope system 1a according to the second embodiment and further different in processing executed. Specifically, in the second embodiment, if a change amount calculated by a first calculation unit 661 is not a third threshold or more, a time interval between temporally successive first fluorescent image and second fluorescent image calculated by the first calculation unit 661 is increased or a region for which a change amount of light intensity is calculated is expanded by increasing number of pixels included in a block (region). However, in the third embodiment, the time interval between the temporally successive first fluorescent image and second fluorescent image calculated by the first calculation unit 661 is increased and the region for which the change amount of the light intensity is calculated is expanded by increasing the number of pixels included in the block based on a light intensity level of a fluorescent wavelength component in a fluorescent image. In the following, the configuration of the endoscope system according to the third embodiment will be described first, and then the processing executed by the endoscope system according to the third embodiment will be described. The same elements as those of the endoscope system 1 according to the first embodiment will be denoted by the same reference signs, and the explanation thereof will be omitted.

Configuration of Endoscope System

Figure 15:
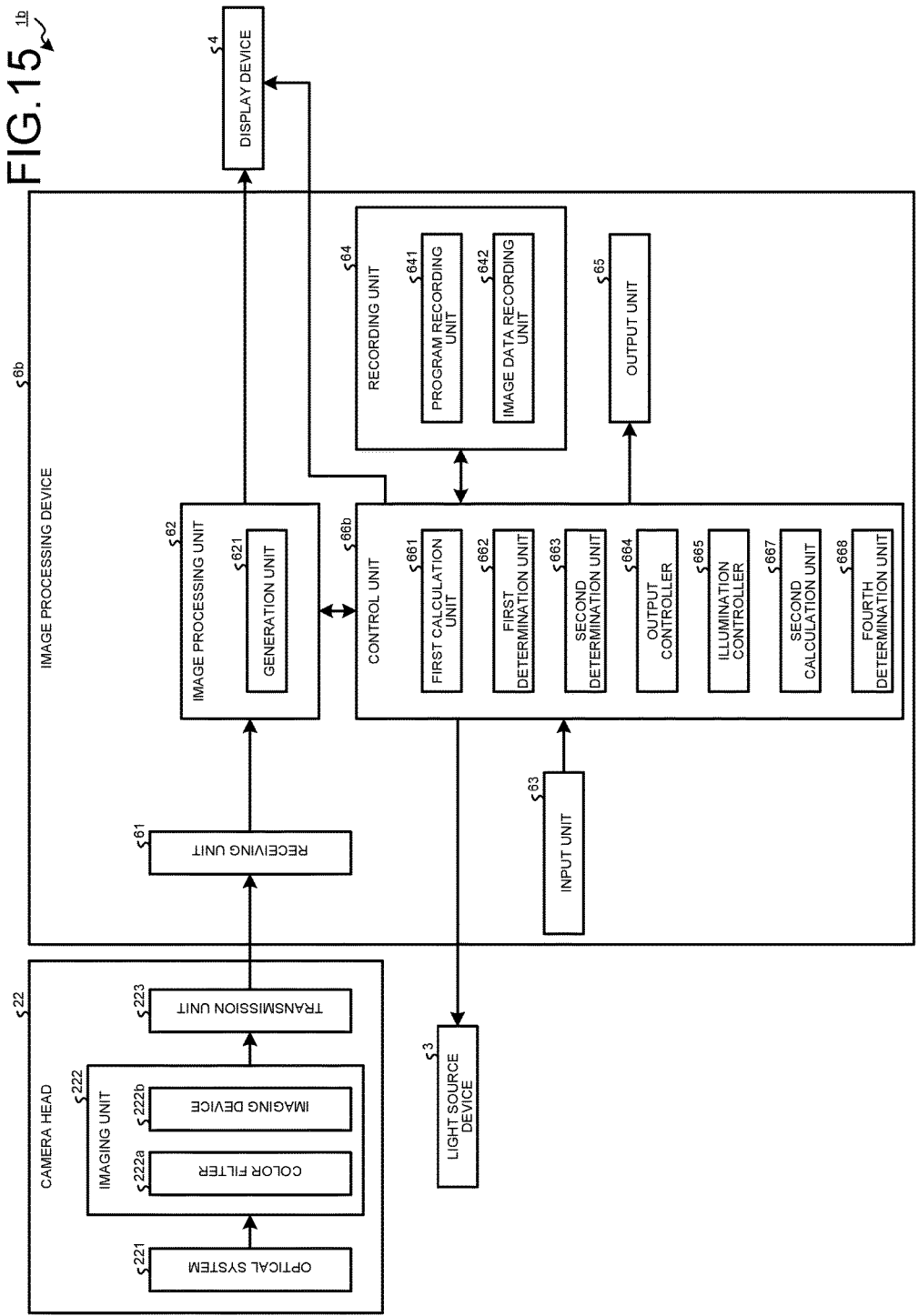
FIG. 15 is a block diagram illustrating a functional configuration of an endoscope system according to a third embodiment of the present invention.

FIG. 15 is a block diagram illustrating a functional configuration of the endoscope system according to the third embodiment of the present invention. An endoscope system 1b illustrated in FIG. 15 includes an image processing device 6b instead of the image processing device 6 of the endoscope system 1 according to the first embodiment. The image processing device 6b includes a control unit 66b instead of the control unit 66 of the image processing device 6 according to the first embodiment. Furthermore, the control unit 66b includes a second calculation unit 667 and a fourth determination unit 668 in addition to the configuration of the control unit 66 according to the first embodiment.

The second calculation unit 667 determines a light intensity level of a fluorescent wavelength component based on fluorescent image data generated by a generation unit 621.

The fourth determination unit 668 determines whether the light intensity level of the fluorescent wavelength component calculated by the second calculation unit 667 is a fourth threshold or more.

Processing of Endoscope System

Figure 16:
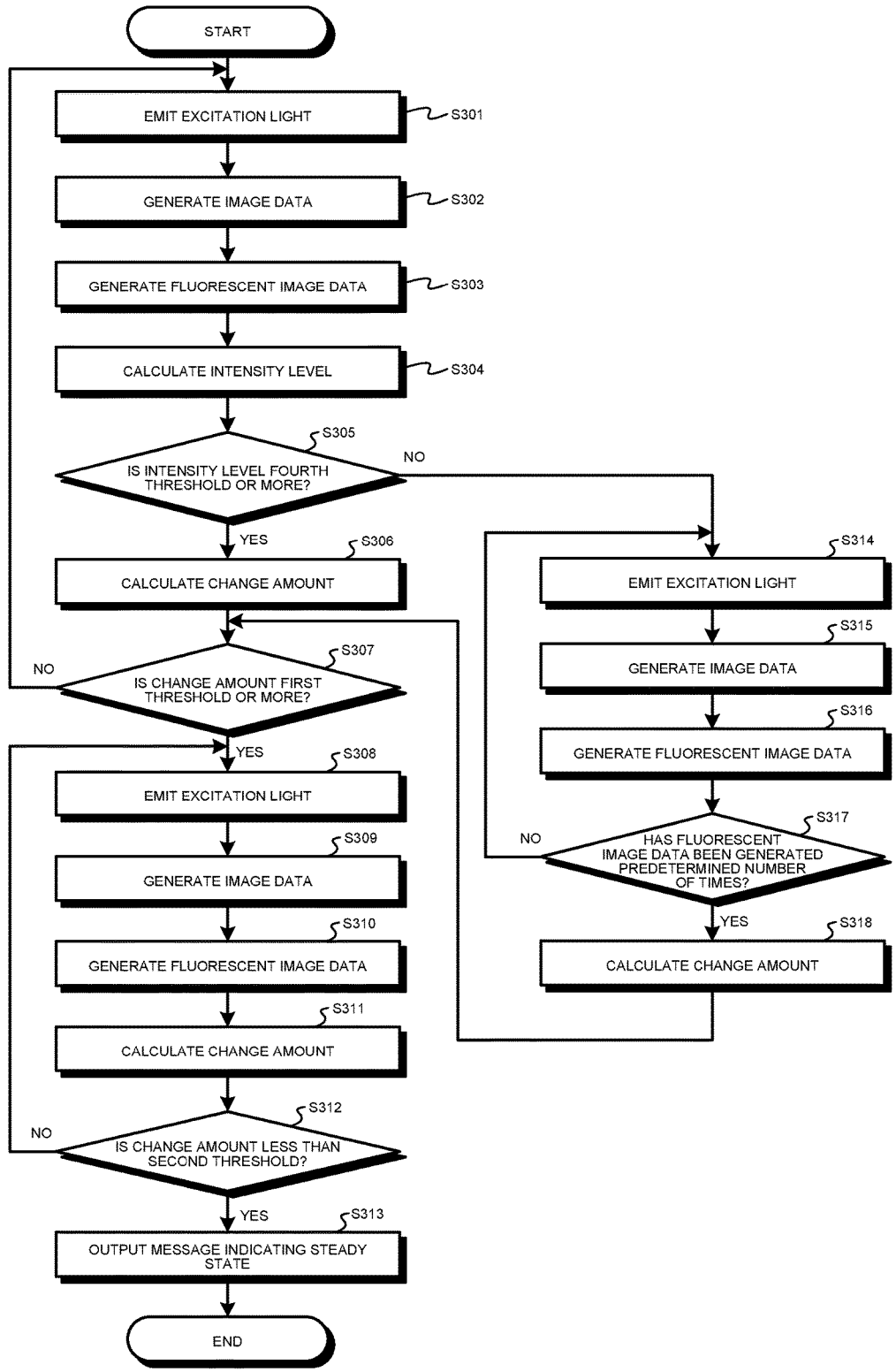
FIG. 16 is a flowchart illustrating an outline of processing executed by the endoscope system according to the third embodiment of the present invention.

Next, processing executed by the endoscope system 1b will be described. FIG. 16 is a flowchart illustrating an outline of the processing executed by the endoscope system 1b.

In FIG. 16, Steps S301 to S303 correspond to above-described Steps S101 to S103 in FIG. 7 respectively.

In Step S304, the second calculation unit 667 calculates the light intensity level of the fluorescent wavelength component based on the fluorescent image data generated by the generation unit 621

Subsequently, the fourth determination unit 668 determines whether the light intensity level of the fluorescent wavelength component calculated by the second calculation unit 667 is the fourth threshold or more (Step S305). If the fourth determination unit 668 determines that the light intensity level of the fluorescent wavelength component calculated by the second calculation unit 667 is the fourth threshold or more (Step S305: Yes), the endoscope system 1b proceeds to Step S306 described later. In contrast, if the fourth determination unit 668 determines that the light intensity level of the fluorescent wavelength component calculated by the second calculation unit 667 is not the fourth threshold or more (Step S305: No), the endoscope system 1b proceeds to Step S313 described later.

Figure 17:
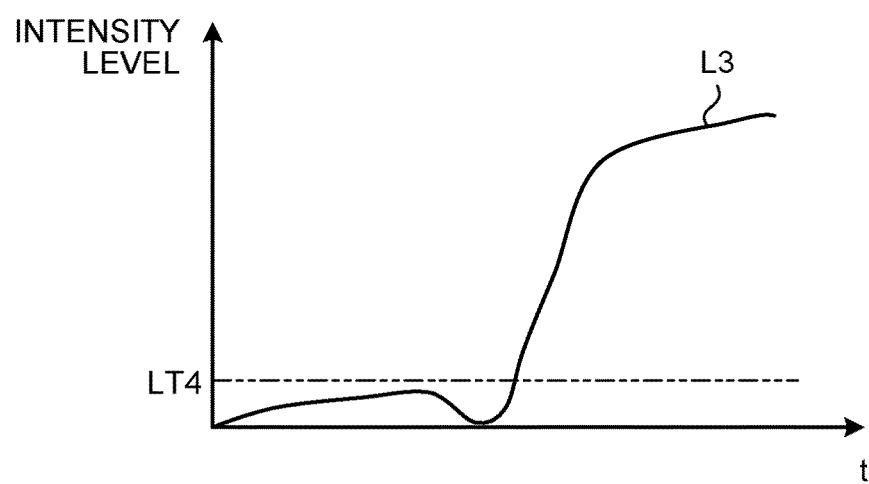
FIG. 17 is a diagram schematically illustrating exemplary temporal change of a light intensity level of a fluorescent wavelength component calculated by a second calculation unit according to the third embodiment of the present invention.

FIG. 17 is a diagram schematically illustrating exemplary temporal change of the light intensity level of the fluorescent wavelength component calculated by the second calculation unit 667. In FIG. 17, a horizontal axis represents time, and a vertical axis represents an intensity level of the light intensity of the fluorescent wavelength component. In FIG. 17, a curve L3 represents temporal change of the light intensity level of the fluorescent wavelength component calculated by the second calculation unit 667.

As illustrated in FIG. 17, since fluorescence of a fluorescent agent is weak, change of the light intensity level of the fluorescent wavelength component calculated by the second calculation unit 667 may be extremely little. Therefore, in the third embodiment, if the fourth determination unit 668 determines that the light intensity level of the fluorescent wavelength component calculated by the second calculation unit 667 is not equal to or greater than the fourth threshold LT4 indicating noise, a time interval between temporally successive fluorescent image data of a previous frame and fluorescent image data of a current frame calculated by the first calculation unit 661 is increased.

Referring back to FIG. 16, processing from Step S306 will be described.

Steps S306 to S312 correspond to above-described Steps S104 to S110 in FIG. 7 respectively. Steps S314 to S318 correspond to above-described Steps S207 to S211 in FIG. 11, respectively.

According to the third embodiment, if the fourth determination unit 668 determines that the light intensity level of the fluorescent wavelength component calculated by the second calculation unit 667 is not equal to or greater than the fourth threshold indicating noise, the change amount of the light intensity is calculated by increasing the time interval between the temporally successive second fluorescent image and first fluorescent image calculated by the first calculation unit 661. Therefore, even when fluorescence of the fluorescent agent is weak, it is possible to surely notify a user of a steady state.

According to the third embodiment of the present invention, if the fourth determination unit 668 determines that the light intensity level is not the fourth threshold or more, the first calculation unit 661 may calculate a difference of the second fluorescent image from the first fluorescent image while setting the light intensity of the fluorescent wavelength component as an index by increasing the number of pixels included in a block having specified number of pixels, and may calculate a sum of the differences as a change amount.

OTHER EMBODIMENTS

Figure 18:
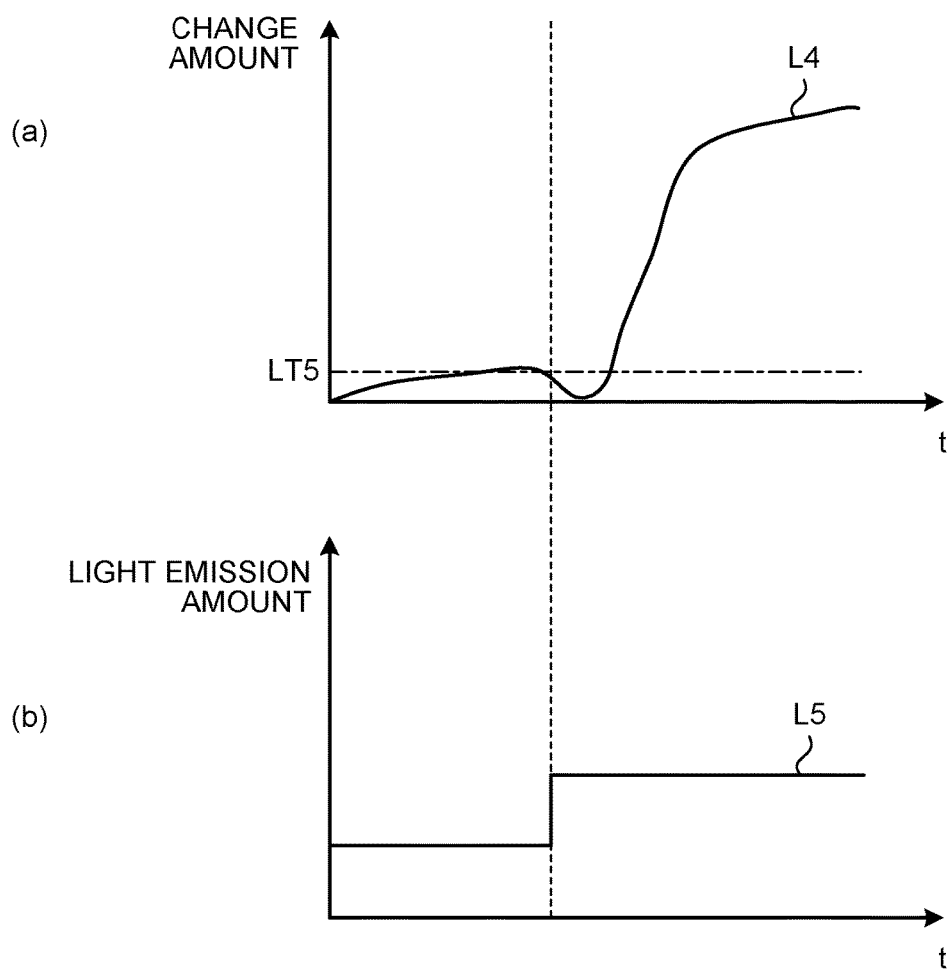
FIG. 18 is a diagram schematically illustrating a light emission amount of excitation light of a light source device by an illumination controller according to a different embodiment of the present invention.

In the first to third embodiments, if a change amount calculated by a first calculation unit 661 is a fifth threshold or more, an illumination controller 665 may make a light source device 3 emit excitation light such that a light emission amount of the excitation light by the light source device 3 is increased. Specifically, as illustrated in (a) of FIG. 18, if a curve L4 representing temporal change of the change amount by the first calculation unit 661 is not the fifth threshold LT5 or more, the illumination controller 665 causes the light source device 3 to emit the excitation light such that the light emission amount of the excitation light is increased as illustrated by a polygonal line L5 in (b) of FIG. 18. Consequently, the light intensity level of fluorescence of the fluorescent agent is increased. Needless to say, the illumination controller 665 may control the light emission amount of the excitation light emitted by the light source device 3 based on the change amount calculated by the first calculation unit 661.

Figure 19:
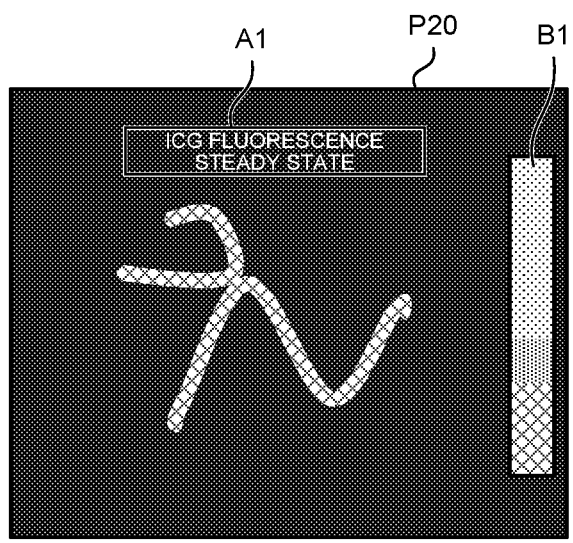
FIG. 19 is a diagram illustrating an exemplary fluorescent image displayed on a display device according to a different embodiment of the present invention.
Figure 20:
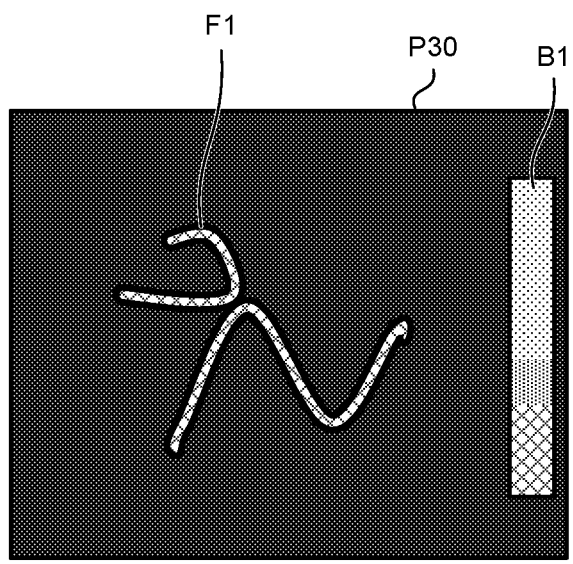
FIG. 20 is a diagram illustrating an exemplary fluorescent image displayed on a display device according to a different embodiment of the present invention.
Figure 21:
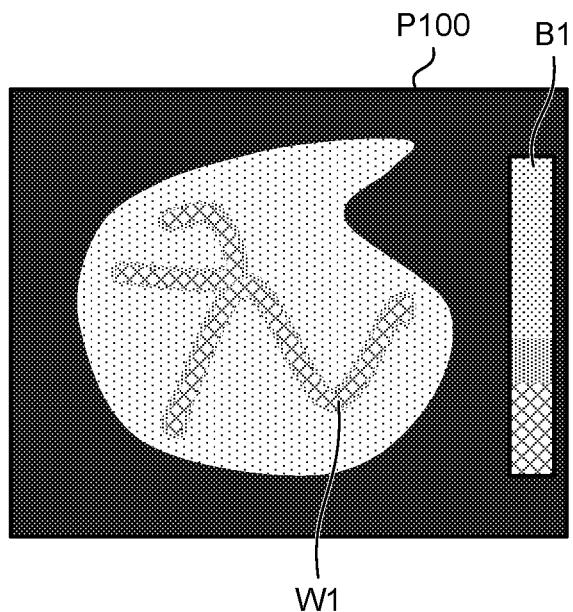
FIG. 21 is a diagram illustrating an exemplary fluorescent image displayed on a display device according to a different embodiment of the present invention.

Furthermore, in the first to third embodiments, a message that fluorescence of a fluorescent agent is in a steady state is notified by the output unit 65, but for example, as illustrated in FIG. 19, an output controller 664 may superimpose information A1 indicating the steady state on a fluorescent image P20 displayed on the display device 4. In this case, the output controller 664 may also superimpose a color bar B1 indicating a state of fluorescence on the fluorescent image P20. Moreover, as illustrated in FIG. 20, the output controller 664 may also cause the display device 4 to display a fluorescent portion in a fluorescent image P30 displayed on the display device 4 by emphasizing an edge of the fluorescent portion with a frame F1. As illustrated in FIG. 21, the output controller 664 may also cause the display device 4 to display the message that fluorescence of the fluorescent agent is in the steady state by superimposing a fluorescent image W1 on a normal color image P100.

Figure 22:
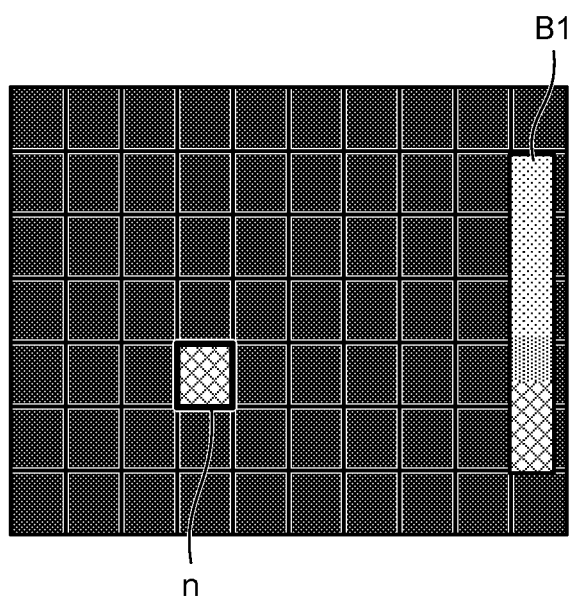
FIG. 22 is a diagram illustrating an exemplary fluorescent image displayed on a display device according to a different embodiment of the present invention.

Furthermore, in the first to third embodiments, the first calculation unit 661 divides a fluorescent image into a plurality of blocks each having specified number of pixels, and calculates a change amount for each of the plurality of blocks, a first determination unit 662 and a second determination unit 663 respectively perform determination, and the output controller 664 causes the output unit 65 to output, for each of the blocks, the message that fluorescence of the fluorescent agent is in the steady state. Needless to say, as illustrated in FIG. 22, the output controller 664 may cause information indicating the steady state to be displayed for each of blocks n in the fluorescent image displayed on the display device 4 in a manner distinguishable from other blocks n. In this case, the output controller 664 may also cause the display device 4 to display a color corresponding to the steady state in the color bar B1.

In the first to third embodiments, each of the endoscope systems 1, 1a, and 1c includes an input unit 63, a recording unit 64, and an illumination controller 665, but these elements may be eliminated in a range without departing from the scope of the invention. Various kinds of inventions can be formed by suitably combining a plurality of elements disclosed in the first to third embodiments. For example, some elements may be eliminated from all of the elements disclosed in the first to third embodiments. Furthermore, the elements described in the first to third embodiments may be suitably combined.

In the embodiments, the term such as "unit" described above may be replaced with "means", "circuit", or the like. For example, the control unit may be replaced with control means or a control circuit.

Furthermore, in the embodiments, image data is transmitted to the image processing device via a transmission cable, but it is not necessarily wired transmission, and wireless transmission may also be employed. In this case, the image data and the like may be transmitted to the image processing device in accordance with a predetermined wireless communication standard (such as Wi-Fi (registered trademark) or Bluetooth (registered trademark)). Needless to say, wireless communication may also be performed in accordance with other wireless communication standards.

In the embodiments, the light source device and the image processing device (processor) are provided separately, but not limited thereto, the image processing device and a light source may be integrated, for example.

In the embodiments, the example of a simultaneous-lighting endoscope has been described, but a sequential-lighting endoscope may also be employed. In some embodiments, an endoscope that can emit not only excitation light but also predetermined narrow band light may also be employed. Moreover, in some embodiments, a flexible endoscope (vertical endoscope), a paranasal sinus endoscope, or a capsule endoscope may also be employed besides a rigid endoscope.

In the embodiments, an endoscope configured to be inserted into a subject has been employed, but for example, a capsule-shaped endoscope or an imaging device adapted to image a subject may also be employed.

In the description for the flowcharts in the present specification, the wording such as "first", "after that", and "subsequently" are used to clarify anteroposterior relations in the processing, but note that the processing order required to implement the present invention is not uniquely determined by the wording. In other words, the order of processing disclosed in the flowcharts of the present specification may be changed in a range having no contradiction.

According to some embodiments, it is possible to assist a doctor in determining whether light emission of a fluorescent agent is in a steady state.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope system, comprising:
   a light source configured to emit excitation light to a subject to which a fluorescent agent has been administered;
   an image sensor configured to continuously image the subject and sequentially generate image data of the subject;
   an integrated circuit or graphics processing unit (GPU) configured to sequentially generate fluorescent image data in accordance with light intensity of a fluorescent wavelength component emitted from the fluorescent agent, based on the image data generated by the image sensor each time the image sensor generates the image data; and
   a processor configured to perform operations including:
      sequentially calculating a change amount of the light intensity based on two sets of temporally successive fluorescent image data each time the fluorescent image data is generated;
      determining whether the sequentially calculated change amount is equal to or greater than a first threshold indicating fluorescence expression;
      determining whether the sequentially calculated change amount is less than a second threshold indicating a steady state of fluorescence after it is determined that the change amount is equal to or greater than the first threshold;
      determining whether the sequentially calculated change amount is equal to or greater than a third threshold for distinguishing noise;
      changing a method for calculating the change amount if it is determined that the change amount is not equal to or greater than the third threshold; and
      outputting a message that fluorescence of the fluorescent agent is in the steady state if it is determined that the change amount is less than the second threshold after it is determined that the change amount is equal to or greater than the first threshold.

2. The endoscope system according to claim 1, wherein the processor is configured to, if it is determined that the change amount is not equal to or greater than the third threshold, increase a time interval between the two sets of temporally successive fluorescent image data used to calculate the change amount.

3. The endoscope system according to claim 1, wherein sequentially calculating the change amount comprises dividing a fluorescent image corresponding to the fluorescent image data into a plurality of blocks each having a specified number of pixels, and calculating, as the change amount, a sum of differences between the plurality of blocks; and
   wherein the processor is configured to, if it is determined that the change amount is not equal to or greater than the third threshold, increase the specified number of pixels to divide the fluorescent image into the plurality of blocks.

4. The endoscope system according to claim 1, wherein sequentially calculating the change amount comprises:
   dividing a fluorescent image corresponding to the fluorescent image data into a plurality of blocks each having a specified number of pixels; and
   calculating the change amount of each of the plurality of blocks.

5. The endoscope system according to claim 1, wherein the processor is configured to perform further operations including controlling a light emission amount of the excitation light emitted by the light source based on the sequentially calculated change amount.

6. The endoscope system according to claim 1, wherein outputting the message that the fluorescence of the fluorescent agent is in the steady state is performed by using one or more of sound, a character, and light.

7. An endoscope system, comprising:
   a light source configured to emit excitation light to a subject to which a fluorescent agent has been administered;
   an image sensor configured to continuously image the subject and sequentially generate image data of the subject;
   an integrated circuit or graphics processing unit (GPU) configured to sequentially generate fluorescent image data in accordance with light intensity of a fluorescent wavelength component emitted from the fluorescent agent, based on the image data generated by the image sensor each time the image sensor generates the image data; and
   a processor configured to perform operations including:
      sequentially calculating a change amount of the light intensity based on two sets of temporally successive fluorescent image data each time the fluorescent image data is generated;
      determining whether the sequentially calculated change amount is equal to or greater than a first threshold indicating fluorescence expression;
      determining whether the sequentially calculated change amount is less than a second threshold indicating a steady state of fluorescence after it is determined that the change amount is equal to or greater than the first threshold;
      calculating a level of the light intensity of a fluorescent image corresponding to the fluorescent image data;

determining whether the calculated level of the light intensity is equal to or greater than a fourth threshold for distinguishing noise;

changing the method for calculating the change amount if it is determined that the level of the light intensity is not equal to or greater than the fourth threshold; and outputting a message that fluorescence of the fluorescent agent is in the steady state if it is determined that the change amount is less than the second threshold after it is determined that the change amount is equal to or greater than the first threshold.

8. The endoscope system according to claim 7, wherein the processor is configured to, if it is determined that the level of the light intensity is not equal to or greater than the fourth threshold, increase a time interval between the two sets of temporally successive fluorescent image data used to calculate the change amount.

9. The endoscope system according to claim 7, wherein sequentially calculating the change amount comprises dividing a fluorescent image corresponding to the fluorescent image data into a plurality of blocks each having a specified number of pixels and calculating, as the change amount, a sum of differences between the plurality of blocks; and wherein the processor is configured to, if it is determined that the level of the light intensity is not equal to or greater than the fourth threshold, increase the specified number of pixels to divide the fluorescent image into the plurality of blocks.

10. An image processing device configured to be connected to an endoscope having an image sensor configured to image a region of a subject to generate image data, a fluorescent agent having been administered to the subject, and the region having been irradiated with excitation light, the image processing device comprising:

an integrated circuit or graphics processing unit (GPU) configured to sequentially generate fluorescent image data in accordance with light intensity of a fluorescent wavelength component emitted from the fluorescent agent, based on the image data generated by the image sensor each time the image sensor generates the image data; and a processor configured to perform operations including:
sequentially calculating a change amount of the light intensity based on two sets of temporally successive fluorescent image data each time the fluorescent image data is generated;

determining determine whether the sequentially calculated change amount is equal to or greater than a first threshold indicating fluorescence expression;

determining whether the sequentially calculated change amount is less than a second threshold indicating a steady state of fluorescence;

determining whether the sequentially calculated change amount is equal to or greater than a third threshold for distinguishing noise;

changing a method for calculating the change amount if it is determined that the change amount is not equal to or greater than the third threshold; and outputting a message that fluorescence of the fluorescent agent is in the steady state if it is determined that the change amount is less than the second threshold after it is determined that the change amount is equal to or greater than the first threshold.

11. An image processing method executed by an image processing device configured to be connected to an endoscope having an image sensor configured to image a region of a subject to generate image data, a fluorescent agent having been administered to the subject, and the region having been irradiated with excitation light, the method comprising:

sequentially generating fluorescent image data in accordance with light intensity of a fluorescent wavelength component emitted from the fluorescent agent, based on the image data generated by the image sensor each time the image sensor generates the image data;

sequentially calculating a change amount of the light intensity based on two sets of temporally successive fluorescent image data each time the fluorescent image data is generated;

determining whether the sequentially calculated change amount is equal to or greater than a first threshold indicating fluorescence expression;

determining whether the sequentially calculated change amount is less than a second threshold indicating a steady state of fluorescence after the change amount is determined to be equal to or greater than the first threshold;

determining whether the sequentially calculated change amount is equal to or greater than a third threshold for distinguishing noise;

changing a method for calculating the change amount if it is determined that the change amount is not equal to or greater than the third threshold; and outputting a message that fluorescence of the fluorescent agent is in the steady state if the change amount is determined to be less than the second threshold after the change amount is determined to be equal to or greater than the first threshold.

12. A non-transitory computer-readable recording medium with an executable program stored thereon for an image processing device configured to be connected to an endoscope having an image sensor configured to image a region of a subject to generate image data, a fluorescent agent having been administered to the subject, and the region having been irradiated with excitation light, the program causing the image processing device to execute operations comprising:

sequentially generating fluorescent image data in accordance with light intensity of a fluorescent wavelength component emitted from the fluorescent agent, based on the image data generated by the image sensor each time the image sensor generates the image data;

sequentially calculating a change amount of the light intensity based on two sets of temporally successive fluorescent image data each time the fluorescent image data is generated;

determining whether the sequentially calculated change amount is equal to or greater than a first threshold indicating fluorescence expression;

determining whether the sequentially calculated change amount is less than a second threshold indicating a steady state of fluorescence after the change amount is determined to be equal to or greater than the first threshold;

determining whether the sequentially calculated change amount is equal to or greater than a third threshold for distinguishing noise;

changing a method for calculating the change amount if it is determined that the change amount is not equal to or greater than the third threshold; and outputting a message that fluorescence of the fluorescent agent is in the steady state if the change amount is determined to be less than the second threshold after the change amount is determined to be equal to or greater than the first threshold.

\* \* \* \* \*